US010316059B2

(12) United States Patent
Bertl et al.

(10) Patent No.: US 10,316,059 B2
(45) Date of Patent: Jun. 11, 2019

(54) SEPARATION OF BISPECIFIC ANTIBODIES AND BISPECIFIC ANTIBODY PRODUCTION SIDE PRODUCTS USING HYDROXYAPATITE CHROMATOGRAPHY

(71) Applicant: Hoffmann-La Roche Inc., Little Falls, NJ (US)

(72) Inventors: Sabine Bertl, Iffeldorf (DE); Harald Duerr, Starnberg (DE); Andreas Schaubmar, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 302 days.

(21) Appl. No.: 15/048,308

(22) Filed: Feb. 19, 2016

(65) Prior Publication Data

US 2016/0376304 A1 Dec. 29, 2016

Related U.S. Application Data

(63) Continuation of application No. PCT/EP2014/067552, filed on Aug. 18, 2014.

(30) Foreign Application Priority Data

Aug. 19, 2013 (EP) .................................... 13180912

(51) Int. Cl.
| | | |
|---|---|---|
| *C07K 16/46* | (2006.01) | |
| *C07K 1/22* | (2006.01) | |
| *C07K 1/18* | (2006.01) | |
| *B01D 15/38* | (2006.01) | |
| *C07K 1/16* | (2006.01) | |
| *C07K 16/00* | (2006.01) | |
| *C07K 16/22* | (2006.01) | |
| *C07K 16/24* | (2006.01) | |
| *C07K 16/28* | (2006.01) | |
| *B01D 15/36* | (2006.01) | |

(52) U.S. Cl.
CPC .............. *C07K 1/18* (2013.01); *B01D 15/362* (2013.01); *B01D 15/3809* (2013.01); *C07K 1/22* (2013.01); *C07K 16/00* (2013.01); *C07K 16/22* (2013.01); *C07K 16/244* (2013.01); *C07K 16/2863* (2013.01); *C07K 16/2875* (2013.01); *C07K 16/468* (2013.01); *C07K 2317/31* (2013.01); *C07K 2317/51* (2013.01); *C07K 2317/52* (2013.01); *C07K 2317/55* (2013.01); *C07K 2317/66* (2013.01)

(58) Field of Classification Search
None
See application file for complete search history.

(56) References Cited

U.S. PATENT DOCUMENTS

| | | | |
|---|---|---|---|
| 2012/0077961 A1 | 3/2012 | Gagnon et al. | |
| 2012/0202975 A1* | 8/2012 | Cummings | B01D 15/361 |
| | | | 530/388.1 |
| 2013/0317200 A1* | 11/2013 | Elson | C07K 16/00 |
| | | | 530/387.3 |
| 2014/0081000 A1* | 3/2014 | Neumann | A61K 39/39591 |
| | | | 530/387.1 |

FOREIGN PATENT DOCUMENTS

| | | |
|---|---|---|
| WO | 2010/102251 A1 | 9/2010 |
| WO | 2011/117329 A1 | 9/2011 |
| WO | 2011/117330 A1 | 9/2011 |
| WO | 2012/024400 A2 | 2/2012 |
| WO | 2013/088259 A2 | 6/2013 |

OTHER PUBLICATIONS

Atwell et al., "Stable Heterodimers from Remodeling the Domain Interface of a Homodimer using a Phage Dispaly Library" Journal of Mol. Biol. 270:26-35 ( 1997).
Ford et al., "Affinity purification of novel bispecific antibodies recognising carcinoembryonic antigen and doxorubicin" Journal of Chromatography B (XP004232827), 754(2):427-435 (Apr. 25, 2001).

(Continued)

*Primary Examiner* — Daniel E Kolker
*Assistant Examiner* — James L Rogers
(74) *Attorney, Agent, or Firm* — Steven Cui

(57) ABSTRACT

The present invention is directed to methods comprising the use of hydroxyapatite chromatography to separate a bispecific antibody from a solution that also comprises one or more byproducts specific to bispecific antibody production. Byproducts specific to the production of bispecific antibodies (bispecific antibody specific byproducts, "BASB") include fragments of the bispecific antibody and heavier molecular weight variants of the antibody, wherein the fragment and/or variant comprises an Fc domain but does not exhibit affinity for the two different epitopes and/or antigens as exhibited by the desired bispecific antibody. Thus, the methods of the present invention comprise the separation of a bispecific antibody from one or more of its BASB. The hydroxyapatite chromatography methods of the invention may be used alone or may be further combined with standard purification processes and unit operations as is known in the art to achieve any level of purity of bispecific antibody necessary, e.g., for therapeutic and/or diagnostic applications.

11 Claims, 19 Drawing Sheets

(56) References Cited

OTHER PUBLICATIONS

Gagnon et al., "Practical issues in the industrial use of hydroxyapatite for purification of monoclonal antibodies" 232nd National Meeting of the Americal Chemical Society, San Francisco (XP055062520), (Sep. 2006).
Gagnon, "Monoclonal antibody purification with hydroxyapatite" New Biotechnol (XP002610667), 25(5):287-293 (Jun. 2009).
Geisse, S. et al., "Eukaryotic Expression Systems: A comparison" Protein Expression and Purification 8:271-282 ( 1996).
IPRP of PCT/EP2014/067552.
ISR and Written Opinion of PCT/EP2014/067552.
Kaufman, "Overview of Vector Design for Mammalian Gene Expression" Mol Biotechnol 16:151-160 ( 2000).
Makrides, S., et al., "Components of Vctors for Gene Transfer and Expression in mammalian cells" Protein Expression and Purification 17:183-202 ( 1999).
Milstein and Cuello, "Hybrid hybridomas and their use in immunohistochemistry" Nature 305:537-540 (Oct. 6, 1983).
Ridgway et al., "'Knobs-into-holes' engineering of antibody CH3 domains for heavy chain heterdimerization" Protein Engineering 9(7):617-621 ( 1996).
Schaefer et al., "Immunoglobulin domain crossover as a generic approach for the production of bispecific IgG antibodies" Proceedings of the National Academy of Sciences 108(27):11187-11192 (Jul. 5, 2011).
Suresh et al., "Bispecific monoclonal antibodies from hybrid hybridomas" Method Enzymol 121:210-228 ( 1986).
Tarditi et al., "Selective high-performance liquid chromatographic purification of bispecific monoclonal antibodies" Journal of Chromatography (XP002981686), 599:13-20 ( 1992).
Vijayalakshmi, "Antibody purification methods" Appl Biochem Biotech 75:93-102 ( 1998).
Werner, R., et al., "Appropriate mammalian expression systems for biopharmaccuticals" Drug Research 48:870-880 ( 1998).
Tada, H. et al., "Production and application of bispecific monoclonal antibodies" Physico-chemical biology 33(1):39-49 (1989).

\* cited by examiner

SEPARATION OF BISPECIFIC ANTIBODIES AND BISPECIFIC ANTIBODY PRODUCTION SIDE PRODUCTS USING HYDROXYAPATITE CHROMATOGRAPHY

CROSS REFERENCE TO RELATED APPLICATIONS

This application is a continuation of International Application No. PCT/EP2014/067552 having an international filing date of Aug. 18, 2014, the entire contents of which are incorporated herein by reference, and which claims benefit under 35 U.S.C. § 119 to European Patent Application No. 13180912.1 filed on Aug. 19, 2013.

FIELD OF THE INVENTION

The present invention is directed to methods comprising the use of hydroxyapatite chromatography to separate a bispecific antibody from a solution that also comprises one or more byproducts specific to bispecific antibody production. Byproducts specific to the production of bispecific antibodies (bispecific antibody specific byproducts, "BASB") include fragments of the bispecific antibody and heavier molecular weight variants of the antibody, wherein the fragment and/or variant comprises an Fc domain but does not exhibit affinity for the two different epitopes and/or antigens as exhibited by the desired bispecific antibody. Thus, the methods of the present invention comprise the separation of a bispecific antibody from one or more of its BASB. The hydroxyapatite chromatography methods of the invention may be used alone or may be further combined with standard purification processes and unit operations as is known in the art to achieve any level of purity of bispecific antibody necessary, e.g., for therapeutic and/or diagnostic applications.

BACKGROUND OF THE INVENTION

The therapeutic potential of bispecific antibodies has long been recognized. Bispecific antibodies offer an IgG like platform that is able to bind two antigens or two epitopes simultaneously. Thus, bispecific antibodies offer a potential tool to modulate the interaction of at least two molecules and/or the interaction of at least two systems comprising the molecules. Such modulation may be, for example, modulation of the interaction of two cells where the recognized antigen, antigens and/or epitopes are expressed on the surface of the cells. Examples of the therapeutic use of bispecific antibodies include, for example, the modulation of cell signaling (e.g., by promoting or interfering with the interaction of desired surface receptors or ligands) and cancer therapies (e.g., aiding in the targeting of immune cells to cancer cells).

Despite the interest in the therapeutic use of bispecific antibodies, their commercial production has proven problematic. Early attempts focused on the fusion of two hybridoma cell lines each expressing monospecific, bivalent antibodies ("quadroma technology", see, e.g., Milstein and Cuello, *Nature* 305(1983), 537-540). Although the quadroma expressed antibody molecules, it was immediately apparent that the expressed molecules contained varying combinations of the two parental heavy and two parental light chains. The simultaneous expression of all four parental chains lead to a mixture of 10 different variants of almost identical molecules, wherein only 1 of the 10 (i.e., only a minor fraction of all molecules expressed) contained the properly paired heavy and light chains necessary to exhibit the desired bispecific activity (see, e.g., Suresh et al., *Methods Enzymol.* 121(1986), 210-228). Accordingly, attention turned to alternate bispecific antibody-based constructs in an attempt to eliminate the production problems, e.g., single-chain fusions of antibody variable domains. However, many of these formats differ significantly from the archetypical antibody structure and were found to exhibit therapeutic disadvantages such as poor pharmacokinetic properties and/or loss of effector activity (e.g., due to absence of Fc domains). Further, many constructs also exhibited a tendency to aggregate and an increased potential for immunogenicity due to the presence of non-human or artificial domains such as linker regions.

In view of the limitation of alternate bispecific formats, and in spite of the production difficulties, interest in bispecific antibodies having the archetypical antibody architecture remains (in particular, IgG like architecture). Principally, two problems arise during the production of a desired bispecific antibody having IgG like architecture. Because such a molecule requires the proper association of 2 different heavy chains and 2 different light chains, it is necessary (1) to induce hetero-dimerization of the two different heavy chains as a preferred reaction over homo-dimerization, and (2) to optimize the discrimination among the possible light-chain/heavy-chain combinations interactions such that the expressed molecule contains only the desired light-chain/heavy-chain interactions. These two issues have effectively been solved.

First, the hetero-dimerization of the two different heavy chains has been shown to be promoted over homo-dimerization interactions by the use of "knobs into holes" or "KiH" methodology. In KiH methodology, large amino acid side chains are introduced into the CH3 domain of one of the heavy chains, which side chains fit into appropriately designed cavities in the CH3 domain of the other heavy chain (see, e.g., Ridgeway et al., *Protein Eng.* 9(1996), 617-621 and Atwell et al., *J. Mol. Biol.* 270(1997), 677-681). Thus, heterodimers of the heavy chains tend to be more stable than either homodimer, and form a greater proportion of the expressed polypeptides.

Second, the association of the desired light-chain/heavy-chain pairings can be induced by modification of one Fab of the bispecific antibody (Fab region) to "swap" the constant or constant and variable regions between the light and heavy chains. Thus, in the modified Fab domain, the heavy chain would comprise, for example, $CL-V_H$ or $CL-V_L$ domains and the light chain would comprise $CH_1-V_L$ or $CH_1-V_H$ domains, respectively. This prevents interaction of the heavy/light chain Fab portions of the modified chains (i.e., modified light or heavy chain) with and the heavy/light chain Fab portions of the standard/non-modified arm. By way of explanation, the heavy chain in the Fab domain of the modified arm, comprising a CL domain, does not preferentially interact with the light chain of the non-modified arm/Fab domain, which also comprises a CL domain (preventing "improper" or undesired pairings of heavy/light chains). This technique for preventing association of "improper" light/heavy chains is termed "CrossMab" technology and, when combined with KiT technology, results in remarkably enhanced expression of the desired bispecific molecules (see, e.g., Schaefer et al., *PNAS* 108(2011), 11187-11192). Alternately or additionally, one arm of the antibody may be modified such that the Fab domain is a scFab or scFv, leaving only one "free" light chain in the system.

Despite the recent advantages in the expression of bispecific antibodies, use of the molecules remains constrained due to the formation of byproducts specifically associated with their production (bispecific-antibody specific byproducts, "BASB") and the problems associated with BASB separation from the desired molecules. As compared to the purification of standard antibodies, the economic purification of bispecific antibodies from production media represents unique challenges. The production of a standard antibody relies on the dimerization of identical heavy-chain/light-chain subunits. In contrast, the production of a bispecific antibody requires the dimerization of two different heavy-chain/light-chain subunits, each comprising a different heavy chain as well as a different light chain. Thus, bispecific antibody production requires the proper interaction of up to four peptide chains. Accordingly, chain mispairings (e.g., homo-dimerization of identical heavy chain peptides or improper heavy-chain/light-chain associations) are often observed, as is incomplete protein assembly due to unbalanced expression of the different antibody chains. Commonly observed BASB include ½ antibodies (comprising a single heavy-chain/light-chain pair) and ¾ antibodies (comprising a complete antibody lacking a single light chain). Additional BASB may be observed depending on the bispecific format used. For example, where one variable domain of the bispecific antibody is constructed as a single-chain Fab (scFab), a 5/4 antibody by-product (comprising an additional heavy or light chain variable domain) may be observed. Such corresponding byproducts are not normally seen in standard antibody production.

Moreover, BASB may exhibit particularly disadvantageous activity should they remain in the final purified product. With respect to standard antibodies, i.e., monospecific antibodies, it can be seen that the above-described by-products contain at least one functional antigen binding site. Therefore, such a byproduct in a monospecific antibody formulation would likely be partially if not entirely therapeutically functional and, thus, of little concern in any purification scheme. In contrast, BASB represent impurities that, depending on bispecific format, could negatively impact the activity of the desired bispecific formulation. Thus, their separation from the desired molecule during purification becomes critical. For example, the functionality of the bispecific molecule may depend on a single molecule exhibiting binding activity to two different antigens. Where a molecule exhibits binding activity to only one target antigen (e.g., as in a ½ or ¾ antibody as described above), its binding to this target antigen would block the binding of a fully functional bispecific antibody, potentially antagonizing the desired activity of the bispecific molecule. At the very least, the monospecific byproducts of bispecific antibody production would likely reduce efficacy of the final bispecific formulation if not separated. Additionally, many of the BASB as described herein, having exposed regions that normally promote peptide-peptide interaction, exhibit a tendency to immunogenicity and aggregation.

Unfortunately, most commercial antibody production and purification schemes are unsuitable or incapable of separating bispecific antibodies from the above-described specific byproducts. Standard antibody purification schemes usually involve at least two distinct modes of chromatography, that is, usually employ at least two chromatographic mechanisms to separate the desired immunoglobulin(s) from byproducts/impurities. The first mode is usually an affinity-based chromatography that utilizes a specific interaction between the protein to be purified (i.e., the protein of interest) and an immobilized capture reagent. Because affinity reagents may represent the most expensive portion of a purification scheme, it is desirable to reduce the use of affinity ligands and/or to maximize applicability of a particular scheme (and affinity reagent) across a number of products. The most commonly used affinity ligand in immunoglobulin purification (and applicable to a wide range of immunoglobulin-based products) are the Fc-binding or constant domain-binding agents such as Protein A, Protein G, Protein L, KappaSelect™ and LambdaFabSelect™. However, the separation activity of these Fc- or constant domain-binding agents is based on the presence of an Fc-, κ-, and/or λ-domains, which, importantly, are shared by the bispecific antibody and its specific byproducts (i.e., BASB). Accordingly, Fc- or constant domain-affinity ligands alone are insufficient to purify bispecific antibodies from the BASB, and the implementation of additional affinity based purifications and/or molecule specific (i.e., antigen-specific) purification would likely lead to economically prohibitive schemes.

Further, based on the understanding in the art prior to the present invention, the addition of other common purification processes used in commercial antibody processing schemes would also not be believed sufficient to satisfactorily separate bispecific antibodies from BASB. The most common purification processes used in conjunction with affinity chromatography for commercial antibody purification are standard chromatography methods that separate the protein of interest from undesired byproducts/impurities based on differences in size, charge (e.g., isoelectric point or "IEP"), solubility, and/or degree of hydrophobicity. Such methods include ion exchange chromatography, size exclusion chromatography, immobilized metal affinity chromatography, and hydroxyapatite chromatography. However, these common chromatography processes using standard protocols are unsuitable for the separation of bispecific antibody from BASB: size exclusion chromatography is not economically feasible for large-scale purifications and the differences in IEP between the bispecific antibody and BASB were believed in large part too small for their separation by ion-exchange chromatography.

Therefore, known methods for the separation of antibodies from solutions comprising by-products specific to their production (e.g., Fc containing antibody fragments) are ineffective for the purification of bispecific antibodies and/or may be undesirable for economic reasons (e.g., the use of additional affinity chromatography steps). Accordingly, there is a need for new and/or improved schemes for the purification of bispecific antibodies from production solutions (and, in particular from BASB contained therein), which schemes are able to meet the requirements of the biotechnology industry for the production of diagnostic and therapeutic products (e.g., demonstrating effective cost, throughput and product purity).

SUMMARY OF THE INVENTION

The present invention is directed to methods using hydroxyapatite chromatography for the separation of a bispecific antibody from a solution containing the bispecific antibody and one or more byproducts specific to the production (e.g., recombinant production) of the bispecific antibody. The byproducts specific to the production (e.g., recombinant production) of bispecific antibodies (also referenced herein as bispecific antibody specific byproducts, "BASB") are higher or lower molecular weight polypeptide variants of the bispecific antibody that lack the desired bispecific activity. For example, the BASB may exhibit specificity for only one of the two epitopes or antigens recognized by the bispecific antibody and/or may exhibit greatly reduced affinity for one or both of the epitopes or antigens recognized by the bispecific antibody. Typical BASB include (i) fragments of the bispecific antibody (i.e., lower molecular weight peptides or polypeptide variants), which include but are not limited to ½ antibodies (having a single heavy chain/light chain pair) and ¾ antibodies (having a hetero- or homo-dimer of antibody heavy chains and a single antibody light chain); and (ii) higher molecular weight polypeptide variants, which include but are not limited to 5/4 antibodies (having a hetero dimer of antibody heavy chains (one of which comprising an antibody scFab or scFv fragment) and two antibody light chains) (see, e.g., FIG. 1). In particular, the methods of the invention are directed to the separation of a bispecific antibody comprising an Fc domain from one or more BASB, which one or more BASB also comprise an Fc domain.

The present inventors have surprisingly discovered that the hydroxyapatite chromatographic methods as described herein can separate a desired bispecific antibody comprising an Fc domain from one or more BASB also comprising an Fc domain in a product feed stream. The methods of the invention may be therefore particularly useful in combination with standard antibody purification schemes that otherwise comprise unit operations insufficient to separate the bispecific antibody from the BASB. The methods described herein may also be particularly useful in combination with standard antibody purification processes to bring the final product stream (containing the bispecific antibody) to final formulation and/or purity.

The invention is directed to a method of separating a bispecific antibody comprising an Fc domain from a solution containing the bispecific antibody, which method comprises (a) contacting the solution with a hydroxyapatite chromatography medium, (b) adsorbing the bispecific antibody to the hydroxyapatite chromatography medium and (c) eluting the bispecific antibody from the hydroxyapatite medium in the presence of chloride ions, wherein the solution containing the bispecific antibody further contains or comprises (i) one or more fragments of the bispecific antibody (which fragments also comprise an Fc domain) and/or (ii) one or more polypeptides having a molecular weight greater than the molecular weight of the bispecific antibody and comprising at least one of the two heavy chains of said bispecific antibody (which one or more polypeptides also comprise an Fc domain). As such, the invention also encompasses the use of hydroxyapatite chromatography medium for the separation of a bispecific antibody comprising an Fc domain from a solution containing the bispecific antibody, which use comprises (a) contacting the hydroxyapatite chromatography medium with the solution, (b) adsorbing the bispecific antibody to the hydroxyapatite chromatography medium and (c) eluting the bispecific antibody from the hydroxyapatite medium in the presence of chloride ions, wherein the solution containing the bispecific antibody further contains (i) one or more fragments of the bispecific antibody (which fragments also comprise an Fc domain) and/or (ii) one or more polypeptides having a molecular weight greater than the molecular weight of said bispecific antibody and comprising at least one of the two heavy chains of said bispecific antibody (which one or more polypeptides also comprise an Fc domain).

The solution containing the bispecific antibody and the one or more BASB is contacted with the hydroxyapatite chromatography medium under conditions that allow the binding of the bispecific antibody and/or the bispecific antibody and the one or more BASB to the chromatography medium. Preferably, the conditions suitable for the binding of the bispecific antibody and the one or more BASB are conditions wherein the solution has a low conductivity value. Solutions with low conductivity values suitable for the methods disclosed herein typically have values about or no greater than about 13 mS/cm. Solutions with low conductivity values suitable for the methods disclosed herein may further have conductivity values about or no more than about 10.6 mS/cm, or about or nor more than about 8.5 mS/cm. Non-limiting examples of solutions with low conductivity values include buffered solutions at pH of about 6.5 to 8.0 comprising a concentration of phosphate ions in the range of between about 1 mM to about 20 mM, preferably about 10 mM; a concentration of calcium ions in the range of between about 0.001 mM to about 0.5 mM, preferably about 0.1 mM; and a concentration of chloride ions in the range of between about 10 mM to about 200 mM, preferably about 50 mM. The solution with a low conductivity value for use in the methods of the invention may have a pH value of about 6.5 to 7.5, a phosphate ion concentration of at least 10 mM, a calcium ion concentration of at least 0.1 mM and a chloride ion concentration from about 50 mM to about 500 mM. Alternatively or additionally, the solution with a low conductivity value for use in the methods of the invention may have a pH value of about 6.5 to 7.5, a phosphate ion concentration of about 10 mM, a calcium ion concentration of about 0.1 mM and a chloride ion concentration from about 50 mM to about 500 mM. The phosphate ions in the solution can be provided by any suitable phosphate salt known in the art and/or described herein, or combinations thereof. Non-limiting examples of phosphate salts suitable for use in the solution according to the methods herein include $NaH_2PO_4$, $Na_2HPO_4$, $KH_2PO_4$ and $K_2HPO_4$. The calcium ions in the solution can be provided by any suitable calcium salt known in the art and/or described herein, or combinations thereof. Non-limiting examples of calcium salts suitable for use in the solution according to the methods herein include $CaCl_2$. The chloride ions in the solution can be provided by any suitable chloride salt known in the art and/or described herein, including salts used to provide the calcium ions, or combinations thereof, provided that calcium ion concentrations are maintained in the ranges specified herein. Non-limiting examples of chloride salts suitable for use in the solution according to the methods of the invention include NaCl, and KCl. Exemplary combinations of chloride ion providing salts for use in these embodiments include NaCl, $CaCl_2$, and KCl. In preferred embodiments, the solution containing the bispecific antibody and the one or more BASB at conditions suitable to allow their initial binding to the hydroxyapatite chromatography medium is a solution comprising (in addition to the bispecific antibody and the one or more BASB) about 10 mM $NaH_2PO_4$, about 50 mM NaCl, 20 mM MES, and about 0.1 mM $CaCl_2$ at pH of about 6.5 to 7.5. As is known in the art, the binding buffer alone (without the bispecific antibody and the one or more BASB), including the embodiments specifically recited in this paragraph, can be used as the equilibration buffer for the hydroxyapatite chromatography medium and/or as a wash buffer at one or more stages of the chromatographic process.

The elution of the bispecific antibody is achieved exclusively by increasing the concentration of the chloride ions. The elution is effected with an elution buffer having a low starting conductivity, wherein the concentration of chloride ions is subsequently steadily increased. The conditions for the selection of a binding solution at low conductivity described immediately above (i.e., the solution containing the bispecific antibody and the one or more BASB at conditions that allow their binding to the hydroxyapatite chromatography medium) apply equally to the selection of the starting composition for the elution buffer of the invention (i.e., also having low starting conductivity). Accordingly, the starting composition of the elution buffer may be the same or may be different from the composition of the binding solution/binding buffer described immediately above or otherwise herein. In certain embodiments, the starting composition of the elution buffer is the same as the composition of the binding solution/binding buffer. In other embodiments, the starting composition of the elution buffer is different from the composition of the binding solution/binding buffer. The elution buffer preferably contains both phosphate and chloride ions. In certain embodiments, the elution buffer has a starting composition of about 10 mM $NaH_2PO_4$, about 50 mM NaCl, about 20 mM MES, and about 0.1 mM $CaCl_2$ at pH of about 6.5 to 7.5.

The invention is directed to methods comprising increasing the concentration of the chloride ions in the elution buffer to elute the bispecific antibody from the chromatography medium. The chloride ion concentration may be increased according to a linear gradient, an implemented step gradient (see, e.g., the implemented step gradient of increasing chloride ions represented in FIG. 6), or a combination of these two gradients. The optimization of the gradient to elute the bispecific antibody from the chromatography medium and/or to separate the bispecific antibody from the BASB (i.e., to elute one while the other remains bound to the medium) is within the capability of one of skill in the art in view of the teaching contained herein. The concentration of chloride ions may be increased in the elution buffer by increasing the concentration of one or more chloride salts. Non-limiting examples of chloride salts that may be added to the elution buffer to increase the concentration of chloride ions include NaCl and KCl. As is understood in the field of protein chromatography, the relative concentrations of calcium and phosphate ions must be monitored or evaluated to prevent precipitation of calcium and phosphate from one or more solutions during the processes of the invention. In certain embodiments, the concentration of chloride ions in the elution buffer is increased by increasing the concentration of NaCl. In preferred embodiments, the starting chloride ion concentration of the elution buffer is about 50 mM (which may be provided by one or more chloride salts) and is subsequently increased during the elution to that necessary to elute the bispecific antibody. One of skill in the art may readily determine the maximum concentration of chloride ions necessary for eluting the adsorbed bispecific antibody using routine methods known in the art and according to the teachings and methods described herein. In certain embodiments, the maximum concentration of chloride ions for elution of the bispecific antibody and/or separation of the bispecific antibody from one or more BASB is about 200 mM, 250 mM, 300 mM, 350 mM, 400 mM or 500 mM. An exemplary elution buffer according to the methods of the invention has a starting composition of about 10 mM $NaH_2PO_4$, about 50 mM NaCl, about 20 mM MES, and about 0.1 mM $CaCl_2$ at a pH of about 6.5 to 7.5, wherein the concentration of chloride ions is subsequently increased by increasing the concentration of NaCl according to a linear, stepwise or linear-stepwise gradient to about 500 mM during the elution step.

The elution of the bispecific antibody is preferably achieved in an eluate fraction, which fraction comprises the bispecific antibody but does not comprise at least one of the BASB adsorbed to the hydroxyapatite chromatography medium. The methods of the invention, in particular, allow the separation of a bispecific antibody from at least one BASB thereof, which at least one BASB thereof is a ½ antibody, a ¾ antibody or a 5/4 antibody. In other words, the methods of the invention allow the separation of a bispecific antibody comprising an Fc domain from a solution comprising said bispecific antibody and one or more BASB comprising (a) contacting the solution with a hydroxyapatite chromatography medium, (b) adsorbing the bispecific antibody to the hydroxyapatite chromatography medium and (c) eluting the bispecific antibody from the hydroxyapatite medium in the presence of chloride ions, wherein the eluate fraction of step (c), which comprises the bispecific antibody, does not contain or does not comprise at least one of the one or more BASB and wherein said one or more BASB is a ½ antibody, a ¾ antibody or a 5/4 antibody. Because hydroxyapatite chromatography medium performance can vary in connection with biological molecules (e.g., bispecific antibodies and BASB) as recognized in the art, it is understood that term "separates" and analogous terms and phrases as used throughout this disclosure with reference to the separation and/or purification of the bispecific antibody from one or more BASB are not to be necessarily interpreted as absolute expressions. Rather, as used herein and in accordance with the understanding in the art, the terms are used with an appreciation that the eluted bispecific antibody may be considered separated and/or purified but may comprise some minimal contamination from the at least one of the one or more BASB (which was also originally adsorbed to the hydroxyapatite chromatography medium). Accordingly, as used herein, the terms "separated", "purified", "does not contain" and analogous terms and phrases used in reference to solutions of bispecific antibodies obtained from/by the methods of the invention are used to mean that the total amount of the one or more BASB in the eluate or eluate fraction(s) comprising the bispecific antibody is not more than 10% of the total amount of the bispecific antibody. In preferred embodiments, the terms "separates"/"separated", "purified", "does not contain" and analogous terms and phrases used in reference to solutions of bispecific antibodies obtained from/by the methods of the invention are used to mean that the total amount of the one or more BASB in the eluate or eluate fraction(s) comprising the bispecific antibody is not more than 5% of the total amount of the bispecific antibody. In other embodiments, the eluted bispecific antibody contains less than 4%, less than 3%, less than 2%, less than 1% or no contamination from the at least one of the one or more BASB. Similarly, the phrase "does not comprise" and analogous phrases in connection the one or more BASB and an eluate and/or eluate fraction(s) are not to be understood as absolute expressions. Rather, as understood in the art, the phrases indicate that the eluate fraction(s) is(are) essentially free of the specific one or more BASB, i.e., may contain a minimal amount of the BASB. Accordingly, as used herein, the eluate or eluate fraction(s) comprising the bispecific antibody and not comprising the one or more BASB, may comprise an amount of the one or more BASB that is not more than 5% of the total amount of the bispecific antibody. As used in this paragraph and throughout the description, the relative percentage of the total amount of the one or more BASB as compared to the total amount of the bispecific antibody in the one or more bisepecific antibody-containing fractions can be determined by any method known in the art or described herein. In non-limiting examples, it may be calculated based on a comparison of the amounts determined or estimated from SDS-Page analysis, MS analysis, or from binding analysis based on BIAcore, Octet or ELISA protocols.

The methods of the invention are applicable to any bispecific antibody format known in the art and/or described herein. Accordingly; the bispecific antibody may comprise antibody peptide chains (e.g., a heavy chain and/or light chain), or antigen binding fragments thereof, from any suitable source antibody, including but not limited to antibodies derived from animal sources (e.g., mouse, rat, hamster, guinea pig, rabbit, goat, sheep, dog, horse, cow, monkey, ape and/or chicken antibodies) as well as chimeric, human and humanized antibodies; may comprise peptide chains (e.g., a heavy chain and/or a light chain) having constant domains (e.g., CL, CH1, CH2 and CH3 domain) from any suitable source antibody, including but not limited to suitable animal sources as defined herein and human antibodies; may comprise peptide chains (e.g., a heavy chain and/or a light chain) having one or more constant domains (e.g., one or more CL, CH1, CH2 and CH3 domain) from any suitable source antibody recombinantly fused or chemically conjugated to an antibody fragment that retains its antigen binding function, including but not limited to, scFv, scFab, Fd, dAb, single-heavy-chain-variable domain and single-light-chain-variable domain; and/or may comprise peptide chains (e.g., a heavy and/or light chain) having human or humanized framework domains. In certain embodiments, the bispecific antibody comprising an Fc domain according to the invention is a "knobs-in-holes" ("KiH") bispecific antibody (i.e., comprises two heavy chains designed according to KiH methods as known in the art and/or as described herein). The KiH methodology may or may not be combined with other bispecific antibody design methodologies. Non-limiting examples of such other bispecific antibody design methodologies include methodologies applied to one or more of the variable domains of the bispecific antibody such as CrossMab methodologies and/or fusion of an antigen binding fragment (e.g., scFab) to one or more heavy chain constant domains. The invention also encompasses the use of CrossMab and antigen binding fragment (e.g., scFab) heavy chain fusion methodologies independent of KiH methodologies. Accordingly, the bispecific antibody of the invention may comprise the use of only one of KiH methodology, CrossMab methodology and antigen-binding fragment-heavy chain fusion methodology, or may comprise the use of more than one of these methodologies. For convenience, as used throughout this disclosure, antibodies designed according to KiH, CrossMab and/or antigen-binding fragment-heavy chain fusion methodologies are referenced as "KiH bispecific antibodies", "CrossMab bispecific antibodies" and/or "binding fragment-heavy fusion antibodies", respectively. In certain embodiments of the invention, the bispecific antibody is binding fragment-heavy chain fusion antibody wherein one heavy chain of the bispecific antibody comprises a scFab that is recombinantly fused or chemically conjugated to a hinge-CH2-CH3 region of an antibody heavy chain (i.e., a "scFab bispecific antibody"). In certain embodiments, the bispecific antibody according to the methods of the invention is a KiH bispecific antibody, a CrossMab bispecific antibody, a scFab bispecific antibody, a KiH-CrossMab bispecific antibody or a KiH-scFab bispecific antibody. In certain embodiments, the bispecific antibody according to the methods of the invention is a KiH bispecific antibody, a CrossMab bispecific antibody, a scFab bispecific antibody, a KiH-CrossMab bispecific antibody or a KiH-scFab bispecific antibody, and the methods of the invention separate the bispecific antibody from one or more BASB thereof.

The present invention is not limited to bispecific antibodies having specificity to any particular epitope or antigen, but is applicable to bispecific antibodies generally and, in particular, applicable to bispecific antibodies having an Fc domain. Accordingly, the antibodies of the invention may have specificity for two or more epitopes (which epitopes are on the same or different antigens) and/or have specificity for two or more antigens. Non-limiting examples of antigens for which the bispecific antibody may exhibit specificity include proteins and polypeptides (including, but not limited to, isolated proteins and polypeptides in native conformation; isolated, denatured proteins and polypeptides; proteins and polypeptides expressed on the surface of a cell (including cell receptors and/or cell markers as known in the art or described herein) and soluble proteins and polypeptides as may be found in biological fluids (e.g., blood, serum, urine, and fractionations of such) such as secreted proteins, shed cell receptors and shed cell markers). In certain embodiments, the bispecific antibody according to the methods of the invention has a specificity for one or more of EGFR, IGFR, Ang2, VEGF, TWEAK, IL17, CD3, TNF (TNF-alpha), fibroblast activation protein (FAP), death receptor 5 (DR5), CEA, melanoma-associated chondroitin sulfate proteoglycan (MCSP), folate receptor 1 (FolR1), latent membrane protein 1/2 (LMP 1/2), or other antigen as described in the detailed description. In alternative or additional embodiments, the bispecific antibody according to the methods of the invention has a specificity for any two of EGFR, IGFR, Ang2, VEGF, TWEAK, IL17, CD3, TNF (TNF-alpha), fibroblast activation protein (FAP), death receptor 5 (DR5), CEA, melanoma-associated chondroitin sulfate proteoglycan (MCSP), folate receptor 1 (FolR1), latent membrane protein 1/2 (LMP 1/2), or other antigen as described in the detailed description. In further alternative or additional embodiments, the bispecific antibody according to the methods of the invention has specificity for EGFR and IGFR, Ang2 and VEGF, or TWEAK and IL17.

In certain embodiments, the bispecific antibody according to the methods of the invention is a KiH-CrossMab bispecific antibody having specificity for EGFR and IGFR, wherein the methods of the invention separate the bispecific antibody from a solution comprising it and at least one BASB, wherein the at least one BASB is a ½ antibody and wherein the separation is obtaining an eluate fraction from the hydroxyapatite chromatography medium, which eluate fraction comprises the EGFR-IGFR bispecific antibody but does not comprise the ½ antibody. In a certain aspect of this embodiment, the bispecific antibody is a KiH-CrossMab bispecific antibody having specificity for EGFR and IGFR, wherein the variable domain specific for IGFR is a CrossMab variable domain. In a preferred aspect of this embodiment, the bispecific antibody is a KiH-CrossMab bispecific antibody having specificity for EGFR and IGFR, wherein the variable domain specific for IGFR is a CrossMab variable domain, wherein the one or more BASB is a ½ antibody and wherein the methods of the invention comprise obtaining an eluate fraction from the hydroxyapatite chromatography medium, which eluate fraction comprises the EGFR-IGFR bispecific antibody but does not comprise the ½ antibody.

In certain embodiments, the bispecific antibody according to the methods of the invention is a KiH-scFab bispecific antibody having specificity for Ang2 and VEGF, wherein the methods of the invention separate the bispecific antibody from a solution comprising it and at least one BASB, wherein the at least one BASB is a ½ antibody and wherein the separation is obtaining an eluate fraction from the hydroxyapatite chromatography medium, which eluate fraction comprises the Ang2-VEGF bispecific antibody but does not comprise the ½ antibody. In a certain aspect of this embodiment, the bispecific antibody is a KiH-scFab bispecific antibody having specificity for Ang2 and VEGF, wherein the variable domain specific for Ang2 is a scFab variable domain. In a preferred aspect of this embodiment, the bispecific antibody is a KiH-scFab bispecific antibody having specificity for Ang2 and VEGF, wherein the variable domain specific for Ang2 is a scFab variable domain, wherein the one or more BASB is a ½ antibody and wherein the methods of the invention comprise obtaining an eluate fraction from the hydroxyapatite chromatography medium, which eluate fraction comprises the Ang2-VEGF bispecific antibody but does not comprise the ½ antibody.

In certain embodiments, the bispecific antibody according to the methods of the invention is a KiH-scFab bispecific antibody having specificity for EGFR and IGFR, wherein the methods of the invention separate the bispecific antibody from a solution comprising it and at least one BASB, wherein the at least one BASB is a ½ antibody and wherein the separation is obtaining an eluate fraction from the hydroxyapatite chromatography medium, which eluate fraction comprises the EGFR-IGFR bispecific antibody but does not comprise the ½ antibody. In a certain aspect of this embodiment, the bispecific antibody is a KiH-scFab bispecific antibody having specificity for EGFR and IGFR, wherein the variable domain specific for IGFR is a scFab variable domain. In a preferred aspect of this embodiment, the bispecific antibody is a KiH-scFab bispecific antibody having specificity for EGFR and IGFR, wherein the variable domain specific for IGFR is a scFab variable domain, wherein the one or more BASB is a ½ antibody and wherein the methods of the invention comprise obtaining an eluate fraction from the hydroxyapatite chromatography medium, which eluate fraction comprises the EGFR-IGFR bispecific antibody but does not comprise the ½ antibody.

In certain embodiments, the bispecific antibody according to the methods of the invention is a KiH-scFab bispecific antibody having specificity for TWEAK and IL17, wherein the methods of the invention separate the bispecific antibody from a solution comprising it and at least one BASB, wherein the at least one BASB is a 5/4 antibody and wherein the separation is obtaining an eluate fraction from the hydroxyapatite chromatography medium, which eluate fraction comprises the TWEAK-IL17 bispecific antibody but does not comprise the 5/4 antibody. In a certain aspect of this embodiment, the bispecific antibody is a KiH-scFab bispecific antibody having specificity for TWEAK and IL17, wherein the variable domain specific for TWEAK is a scFab variable domain. In a preferred aspect of this embodiment, the bispecific antibody is a KiH-scFab bispecific antibody having specificity for TWEAK and IL17, wherein the variable domain specific for TWEAK is a scFab variable domain, wherein the one or more BASB is a 5/4 antibody and wherein the methods of the invention comprise obtaining an eluate fraction from the hydroxyapatite chromatography medium, which eluate fraction comprises the TWEAK-IL17 bispecific antibody but does not comprise the 5/4 antibody.

In certain embodiments, the bispecific antibody according to the methods of the invention is a KiH-CrossMab bispecific antibody having specificity for Ang2 and VEGF, wherein the methods of the invention separate the bispecific antibody from a solution comprising it and at least one BASB, wherein the at least one BASB is a ¾ antibody and wherein the separation is obtaining an eluate fraction from the hydroxyapatite chromatography medium, which eluate fraction comprises the Ang2-VEGF bispecific antibody but does not comprise the ¾ antibody. In a certain aspect of this embodiment, the bispecific antibody is a KiH-CrossMab bispecific antibody having specificity for Ang2 and VEGF, wherein the variable domain specific for Ang2 is a CrossMab variable domain. In a preferred aspect of this embodiment, the bispecific antibody is a KiH-CrossMab bispecific antibody having specificity for Ang2 and VEGF, wherein the variable domain specific for Ang2 is a CrossMab variable domain, wherein the one or more BASB is a ¾ antibody and wherein the methods of the invention comprise obtaining an eluate fraction from the hydroxyapatite chromatography medium, which eluate fraction comprises the Ang2-VEGF bispecific antibody but does not comprise the ¾ antibody.

Any of the hydroxyapatite methods disclosed herein, whether described as an aspect and/or embodiment of the invention, and whether described as preferred or not, can be combined with upstream or downstream purification processes described herein and/or otherwise known in the art. Examples of such purification processes that may be combined upstream or downstream with the hydroxyapatite methods disclosed herein include but are not limited to affinity chromatography, size exclusion chromatography, ion exchange chromatography (including anion and cation exchange chromatography), hydrophobic interaction chromatography, other forms of mixed mode chromatography and various filtrations methods as is known in the art. It is within the ability of the skilled person to develop appropriate conditions for integration with the disclosed methods to achieve a particular purification of a bispecific antibody. In non-limiting examples, any of the hydroxyapatite chromatographic methods disclosed herein may be combined with an upstream affinity chromatographic method, wherein the affinity ligand has a specificity for an antibody domain such as the Fc domain, kappa domain or lambda domain (for example, but not limited to, Protein A, Protein G, Protein A/G, Protein L, KappaSelect™ and LambdaFabSelect™ (GE Healthcare Life Sciences, Upsala, SE)). In certain embodiments, the solution containing the bispecific antibody and one or more BASB and that is contacted with the hydroxyapatite chromatography medium according to the methods of the invention, comprises the pooled antibody containing fractions of the eluate from an affinity chromatography medium having specificity for an antibody Fc domain, or an antibody light chain kappa or lambda domain. In further non-limiting examples, the hydroxyapatite chromatographic method according to the invention may be combined with upstream or downstream purification processes, including but not limited to, anion chromatography and cation chromatography. As a non-limiting example, any method, aspect, embodiment or other example of the hydroxyapatite chromatographic methods according to the invention disclosed herein may be combined with upstream or downstream anion or cation chromatography. In a specific example, which may be combined with any method, aspect embodiment or other example disclosed herein, the hydroxyapatite chromatographic methods according to the invention may be combined with upstream or downstream cation chromatography, which cation chromatography may separate the bispecific antibody from one or more contaminant, impurity and/or second BASB. As used herein, the terms "contaminant", "impurity" and analogous terms have their standard meaning known in the art and, in particular, indicate undesired components in a solution containing the bispecific antibody. Non-limiting examples of such undesired components include undesired proteins (for example, but not limited to, homodimers of a heavy chain of the bispecific antibody), undesired small molecules, one or more fragments of the bispecific antibody other than a BASB as described herein, aggregates of the bispecific antibody, and undesired proteins/molecules produced by the cell (whether endogenous or heterologous). As used herein the term "second BASB" and analogous terms refer to a BASB that is not the at least one BASB that is separated from the bispecific antibody by the hydroxyapatite chromatographic methods disclosed herein. Thus, in certain embodiments, the hydroxyapatite chromatographic methods disclosed herein separate a bispecific antibody from a solution containing the bispecific antibody and at least one BASB, wherein the separation is eluting the bispecific antibody from the hydroxyapatite chromatography medium in an elution fraction that contains the bispecific antibody but does not contain the at least one BASB, and wherein the methods are combined with at least one upstream or downstream cation chromatographic method that separates the bispecific antibody from at least one contaminant, impurity and/or second BASB. In a specific example, which may be combined with any method, aspect embodiment or other example disclosed herein, the hydroxyapatite chromatographic method according to the invention may be combined with (1) an upstream affinity chromatographic method, wherein the affinity ligand has a specificity for an antibody domain such as the Fc domain, kappa domain or lambda domain; and (2) an upstream or downstream cation chromatographic method, which cation chromatography separates the bispecific antibody from one or more contaminant, impurity and/or second BASB.

DEFINITIONS

In general, the following words or phrases have the indicated definition when used in the summary, description, examples, and claims.

As used herein, the term "about" in connection with a number indicates ±5% of the number. When used in connection with a measurement performed by a device (e.g., pH as determined by a pH meter) or performed according to a standard method known in the art (e.g., protein concentration of a solution determined by HPLC, UV adsorption, ELISA, standard kits (e.g., colorimetric assay)), "about" indicates a value within the standard error known for such a device or within one standard deviation of the determined value for such a method.

The term "antibody" is used in the broadest sense and specifically covers, for example, single monoclonal antibodies (including agonist, antagonist, and neutralizing antibodies; as well as de-immunized, chimeric, humanized and human antibodies and/or antibodies derived from any suitable animal source (e.g., from mice, rats, hamsters, guinea pigs, rabbits, goats, sheep, dogs, horses, cows, monkeys, apes and/or chickens)), immuno-conjugates, synthetic antibodies, camelized antibodies, single-chain Fvs (scFv), single chain antibodies, Fab fragments, F(ab') fragments, F(ab')$_2$ fragments, disulfide-linked Fvs (sdFv), intrabodies, and epitope-binding fragments of any of the above. In particular, the invention is directed to bispecific antibodies, which, as understood by one of skill in the art and in certain embodiments, is considered comprised of domains from at least two or more different antibodies. Thus, the bispecific antibody of the invention may comprise two different heavy chains (each derived from a different antibody) and two different light chains (each derived from a different antibody), and/or may comprise heavy and light chains each comprising fragments from two or more different antibodies. Thus, the bispecific antibody of the invention may comprise heavy and/or light chains from de-immunized, murine, chimeric, humanized and human antibodies, as well as combinations heavy and/or light chains from de-immunized, murine, chimeric, humanized, human antibodies and fragments thereof (e.g., variable and/or constant domains thereof). The bispecific antibody of the invention may also comprise epitope binding fragments of antibodies (for example, but not limited to single-chain Fvs (scFv), single chain antibodies, Fab fragments, F(ab') fragments, F(ab')$_2$ fragments, and disulfide-linked Fvs (sdFv)), in particular, linked to one or more heavy or light chain constant domains, e.g., a scFv linked to heavy chain CH1/CH2/CH3 domains. In preferred embodiments, the bispecific antibody of the invention comprises an Fc domain. As understood by one of skill in the art, the presence of an Fc domain renders the bispecific antibody amenable to purification using Fc-binding moieties such as, but not limited to, Protein A, Protein G, and/or Protein A/G. As is well recognized in the art, the particular structure and amino acid sequence of the CH1-hinge-CH2-CH3 domains of the heavy chains determines the immunoglobulin type and subclass. The bispecific antibodies of the invention are not in any manner limited to a specific heavy chain structure or amino acid sequence; accordingly, the bispecific antibodies of the invention may be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

"Affinity ligand" as used herein, and with particular respect to a chromatographic process, refers to a moiety that binds selectively or preferentially to a component within the feed or load stream of the process via a specific interaction with a binding site on the moieties (e.g., ligand) and/or component. An immunoglobulin-affinity ligand according to the present invention selectively or preferentially binds the Fc- or other constant domain of an immunoglobulin (e.g., to the κ- or λ-domain of the antibody light chain). Therefore, the "immunoglobulin-affinity ligand" as used herein selectively or preferentially binds to components within the feed or load stream having an Fc-, κ- and/or λ-domain(s). The immunoglobulin-affinity ligand is typically immobilized to a solid phase such as a resin support. Examples of immunoglobulin-affinity ligands that can be bound to the resin support according to the present invention include, but are not limited to Fc-affinity ligands such as, but not limited to, Protein A, Protein G and Protein A/G, and their analogs; as well as affinity ligands that bind to other constant domains of immunoglobulins (such as to the κ- and/or λ-domains) including, but not limited to, KappaSelect™ and Lambda-FabSelect™ (GE Healthcare Life Sciences, Upsala, SE), and their analogs. Methods of binding affinity ligands to solid support materials are well known in the purification art. See, e.g., *Affinity Separations: A Practical Approach* (*Practical Approach Series*), Paul Matejtschuk (Ed.), (Irl Pr: 1997); and *Affinity Chromatography*, Herbert Schott (Marcel Dekker, New York: 1997).

As used herein, the term "between" in connection with the definition of a parameter within a range expressly includes the endpoints of that range. Thus, if the parameter is defined herein as being "between X and Y", it is expressly intended that the parameter may have a value equal to X or greater than X, so long as the value is less than or equal to Y, i.e., is not more than Y. In other words, the values defined by the phrase "between X and Y" and analogous constructions expressly includes the values X and Y.

As used herein, the expressions "cell", "cell line", and "cell culture" are used interchangeably, and all such designations include progeny. In particular, the invention encompasses the separation and/or purification of molecules of interest, i.e., bispecific antibodies, from the products of cells, cell lines and cell cultures. Such products typically include conditioned cell media and/or lysed and homogenized cells and cell cultures (e.g., homogenized cells and cell components within conditioned cell media). The methods of the invention are particularly suited to the processing of products from transgenic cells, cell lines and cell cultures, wherein the transgenic cells, cell lines and cell cultures express the molecule of interest.

It is understood that the methods of the invention relate to the separation, purification and/or processing of a molecule of interest, e.g., a bispecific antibody, from a solution containing the molecule. The solution containing the molecule of interest according to the methods of the present invention includes the feed stream or load stream of a chromatographic process, e.g., the feed or load stream applied to one or more chromatographic unit operations, e.g., as part of a purification scheme. As such, where the solution containing the molecule of interest is cell culture media or a fractionated or clarified part of cell culture media, it is understood that such media is necessarily conditioned cell culture media (so as to comprise the molecule of interest). Therefore, as used herein, the term "cell culture solution" and analogous terms refer to any solution of a biological process or system expected to contain the molecule of interest, including but not limited to, e.g., conditioned cell culture supernatant; clarified conditioned cell culture supernatant; clarified, homogenized/lysed cell cultures, etc.

In certain embodiments the cell culture media is clarified and/or sterilized prior to implementation of the methods disclosed herein. As used herein, the term "clarified" and "clarification" refer to the removal of particulate matter from a solution, including filtration sterilization and/or centrifugation. The term "sterilized" as used herein is understood to be used in connection with a solution containing proteins; accordingly, "sterilization" of such solutions is understood to be preferably effected by filtration and/or centrifugation and not by heat to avoid protein denaturation and/or protein aggregation. Typically, a "clarified"/"sterilized" solution with reference to any cell culture media is a solution that has been filtered through a membrane of not more than about 0.45 μm pore size, and preferably, not more than about 0.22 μm pore size.

The term "chromatography medium" as used herein refers to a solid phase material that is capable of selective binding to one or more components of an applied load fluid as is well known in the art. The invention encompasses, in particular, the use of any hydroxyapatite chromatography medium known in the art and/or defined herein for the processing of the molecule of interest, specifically, a bispecific antibody. The methods of the invention further encompass combination of the hydroxyapatite chromatography with one or more further chromatographic processes (e.g., ion exchange chromatography) as part of a purification scheme for the separation of the molecule of interest, i.e., a bispecific antibody, from one or more byproducts specific to the manufacture of the bispecific antibody, i.e., bispecific antibody specific byproducts ("BASB"). Examples of chromatographic unit operations with which the hydroxyapatite chromatography can be combined according to the methods of the invention include, but are not limited to, chromatographic unit operations comprising the use of solid phases (e.g., resins) that selectively bind to one or more components of a load fluid via cation exchange, anion exchange, hydrophobic interaction, hydrophilic interaction, hydrogen bonding, pi-pi bonding, metal affinity and/or specific binding via biomolecules (e.g., affinity resins comprising immunoglobulins, immunoglobulin fragments, and enzymes). The solid phase can be a porous particle, nonporous particle, membrane, or monolith. It is within the ability of the person of skill in the art to develop appropriate conditions for these additional chromatographic unit operations and to integrate them with the invention disclosed herein to achieve purification of a particular bispecific antibody.

The terms "Fc domain", "Fc region" and analogous terms as used herein refer to the C-terminal region of an IgG antibody, in particular, the C-terminal region of the heavy chain(s) of an IgG antibody, containing the CH2/CH3 domains of the IgG heavy chain. Although the boundaries of the Fc region of an IgG heavy chain can vary slightly, the Fc domain is typically defined as spanning from about amino acid residue Cys226 to the carboxyl-terminus of an IgG heavy chain(s). As is known in the art, the Fc region may be used independently of the remaining antibody architecture, e.g., linked to a second protein to function as a protein tag or to impart functionality typically associated with the Fc region to the second protein (e.g., complement binding activity, FcRn binding etc.). Such second proteins linked (for example, but not limited to, chemical conjugations and recombinant fusions) to the Fc domain include immunoglobulin fragments. As is recognized in the art, in proteins comprising such Fc conjugations or fusions, the Fc-region need not necessarily be the C-terminal region of the protein chain or expressed amino-acid sequence.

The term "byproduct" and analogous terms refer to any objectionable molecule present in the load or feed stream that specifically results from the production of the molecule of interest, i.e., a bispecific antibody, and that is to be separated therefrom during the chromatographic/purification process. With respect to the phrase bispecific antibody specific byproducts, "BASB", the term refers to byproducts containing an Fc-domain that are specific to the recombinant production of bispecific antibodies. Accordingly, a BASB may be a fragment of the bispecific antibody, which fragment comprises an Fc domain, or may be a polypeptide having a molecular weight greater than the molecular weight of the bispecific antibody, which polypeptide comprises at least one of the two heavy chains of the bispecific antibody and further comprises an Fc domain. Depending on the desired bispecific antibody format to be expressed, typical BASB that may be separated from the bispecific antibody according to the methods of the invention include, but are not limited to, ½ antibodies (containing a one antibody light chain/heavy chain pair), ¾ antibodies (containing a heterodimer or a homodimer of antibody heavy chains and a single antibody light chain) and 5/4 antibodies (containing a heterodimer or homodimer of antibody heavy chains (one of which heavy chains may or may not be a scFab-heavy chain fusion as defined herein), a single antibody light chain and a Fab or scFab fragment) (see, FIG. 1).

The methods of the invention also encompass the separation of impurities and/or contaminants other than BASB from solutions containing the bispecific antibody. As used herein, the terms "impurity", "contaminant" and analogous terms refer to any foreign or objectionable molecule, including a biological macromolecule such as a DNA, a RNA, or a protein, other than the molecule of interest that is also present in a load/load fluid containing the molecule of interest. Impurities include, for example, protein variants (including but not limited to, the BASB specifically outlined herein, aggregated proteins, high molecular weight species, low molecular weight species and fragments, and deamidated species); other proteins from host cells that secrete the molecule of interest being purified (host cell proteins); proteins that are part of an absorbent used for affinity chromatography that may leach into a sample during prior purification steps (e.g., Protein A); endotoxins; and viruses.

DETAILED DESCRIPTION

Figure 1:
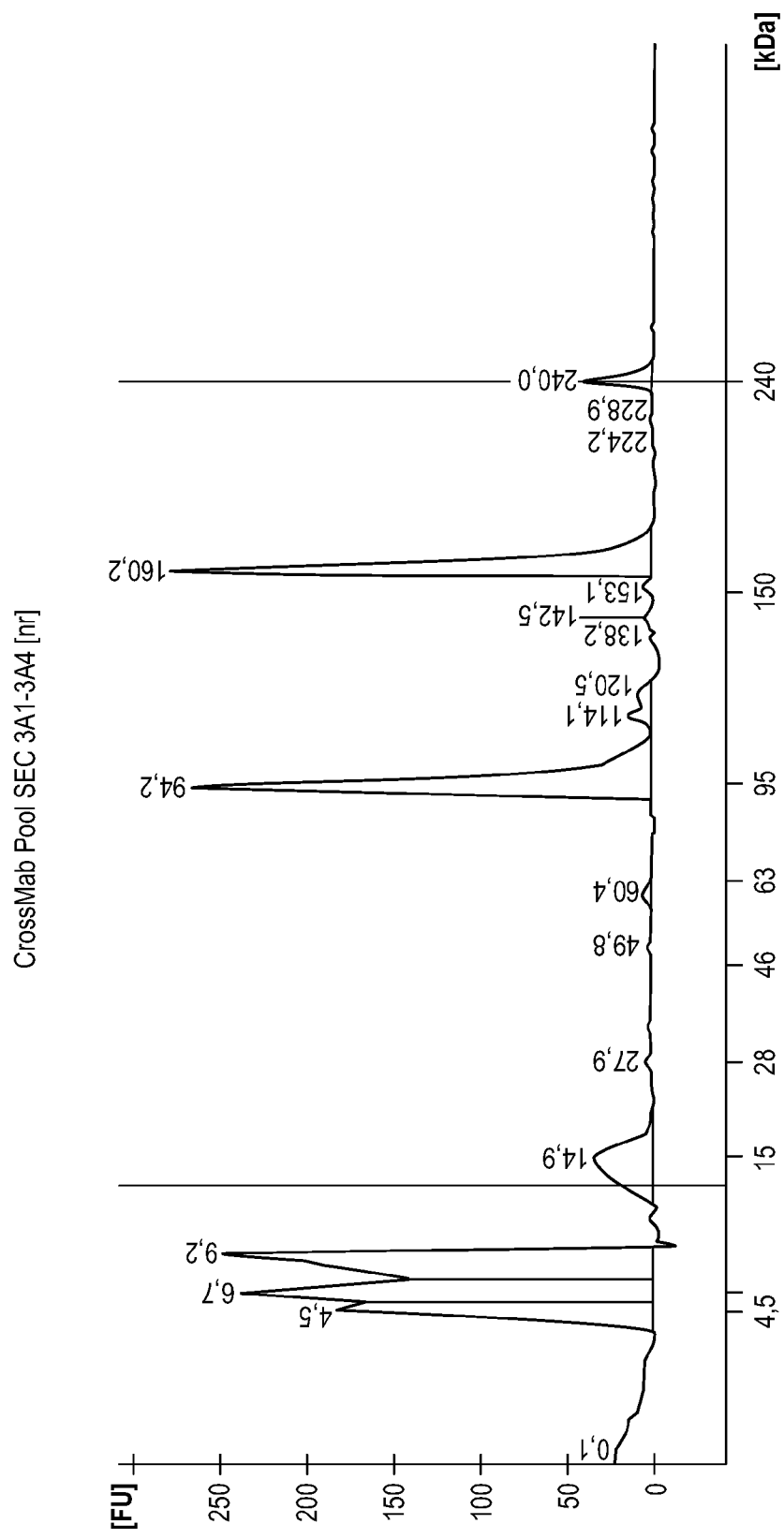
FIG. 1 Non-reducing CE-SDS analysis of production culture supernatant of KiH-CrossMab anti-EGFR/anti-IGFR bispecific antibody, subsequent to Protein A chromatography.

It has surprisingly been discovered that hydroxyapatite chromatography can be used to separate bispecific antibodies from at least one byproduct specific to bispecific antibody production (i.e., from at least one bispecific antibody specific byproduct, "BASB"). Although hydroxyapatite chromatography has been shown in protein purification processes to yield a high degree of purification from impurities such as aggregates, DNA and endotoxins, it has not been demonstrated to separate molecules having IEPs that differ only marginally (see, e.g., Gagnon et al., *Hydroxyapatite as a Capture Method for Purification of Monoclonal Antibodies*, IBC World Conference and Exposition, San Francisco (2006)). Typically, the bispecific antibody and BASB will differ in their IEP values by no more than 0.5 pH, which, prior to the present invention and teaching, were believed too close to be separated using ionic exchange chromatography. Accordingly, attempts to purify bispecific antibodies typically rely on the use of multiple costly affinity steps to ensure the purification of molecules with bispecific activity. In contrast, the present methods offer simplified and/or otherwise improved purification protocols for the separation of a bispecific antibody and at least one BASB.

The BASB as defined herein are fragments of the bispecific antibody comprising an Fc domain, and/or polypeptide variants of the bispecific antibody having a molecular weight greater than the bispecific antibody, which polypeptide variant comprises at least one of the two heavy chains of the bispecific antibody and further comprises an Fc domain. Non-limiting examples of BASB include a ½ antibody, a ¾ antibody and a 5/4 antibody. As such the disclosed hydroxyapatite chromatographic methods may supplement existing antibody purification schemes, which are generally unsuitable or insufficient to separate bispecific antibodies from one or more BASB. The hydroxyapatite chromatographic methods disclosed herein may be used in any process for the separation/purification/isolation of a bispecific antibody from a solution, in particular, wherein the solution comprises one or more BASB. The methods of the invention may be used to separate a bispecific antibody from a solution containing it and one or more (i.e., at least one) BASB, wherein, subsequent to adsorption of the bispecific antibody or bispecific antibody and one or more BASB on the hydroxyapatite medium, the separation comprises obtaining an eluate fraction that contains the bispecific antibody but does not contain the one or more BASB. As described herein, the methods of the invention may be used to separate a bispecific antibody from a solution containing it and one or more (i.e., at least one) BASB, wherein, subsequent to adsorption of the bispecific antibody or subsequent to adsorption of the bispecific antibody and one or more BASB on the hydroxyapatite medium, the separation comprises obtaining an eluate fraction that contains the bispecific antibody but does not contain the one or more BASB wherein the one or more BASB is a ½ antibody, ¾ antibody or a 5/4 antibody. In certain embodiments, the methods of the invention may be used to separate a bispecific antibody from a solution comprising it and one or more (i.e., at least one) BASB, wherein the one or more BASB is a ½ antibody, and, subsequent to adsorption of the bispecific antibody or bispecific antibody and ½ antibody on the hydroxyapatite medium, the separation comprises obtaining an eluate fraction that contains the bispecific antibody but does not contain the ½ antibody. In related or alternative embodiments, the methods of the invention may be used to separate a bispecific antibody from a solution comprising it and one or more (i.e., at least one) BASB, wherein the one or more BASB is a ¾ antibody, and, subsequent to adsorption of the bispecific antibody or bispecific antibody and ¾ antibody on the hydroxyapatite medium, the separation comprises obtaining an eluate fraction that contains the bispecific antibody but does not contain the ¾ antibody. In further related or alternative embodiments, the methods of the invention may be used to separate a bispecific antibody from a solution comprising it and one or more (i.e., at least one) BASB, wherein the one or more BASB is a 5/4 antibody, and, subsequent to adsorption of the bispecific antibody or bispecific antibody and 5/4 antibody on the hydroxyapatite medium, the separation comprises obtaining an eluate fraction that contains the bispecific antibody but does not contain the 5/4 antibody. In further related or alternative embodiments, the methods of the invention may be used to separate a bispecific antibody from a solution comprising it and one or more (i.e., at least one) BASB, wherein the one or more BASB is a ½ antibody and a ¾ antibody, and, subsequent to adsorption of the bispecific antibody or bispecific antibody, ½ antibody and ¾ antibody on the hydroxyapatite medium, the separation comprises obtaining an eluate fraction that contains the bispecific antibody but does not contain one or both of the ½ antibody and ¾ antibody. In further related or alternative embodiments, the methods of the invention may be used to separate a bispecific antibody from a solution comprising it and one or more (i.e., at least one) BASB, wherein the one or more BASB is a ½ antibody and a 5/4 antibody, and, subsequent to adsorption of the bispecific antibody or bispecific antibody, ½ antibody and 5/4 antibody on the hydroxyapatite medium, the separation comprises obtaining an eluate fraction that contains the bispecific antibody but does not contain one or both of the ½ antibody and 5/4 antibody. In further related or alternative embodiments, the methods of the invention may be used to separate a bispecific antibody from a solution comprising it and one or more (i.e., at least one) BASB, wherein the one or more BASB is a ¾ antibody and a 5/4 antibody, and, subsequent to adsorption of the bispecific antibody or bispecific antibody, ¾ antibody and 5/4 antibody on the hydroxyapatite medium, the separation comprises obtaining an eluate fraction that contains the bispecific antibody but does not contain one or both of the ¾ antibody and 5/4 antibody. In further related or alternative embodiments, the methods of the invention may be used to separate a bispecific antibody from a solution comprising it and one or more (i.e., at least one) BASB, wherein the one or more BASB is a ½ antibody, a ¾ antibody and a 5/4 antibody, and, subsequent to adsorption of the bispecific antibody or bispecific antibody, ½ antibody, ¾ antibody and 5/4 antibody on the hydroxyapatite medium, the separation comprises obtaining an eluate fraction that contains the bispecific antibody but does not contain one, two or all of the ½ antibody, ¾ antibody and 5/4 antibody.

Hydroxyapatite [HA] is a crystalline mineral of calcium phosphate with a structural formula of $Ca_{10}(PO_4)_6(OH)_2$. Protein-reactive sites on HA include pairs of positively charged calcium ions (C-sites) and triplets of negatively charged phosphate groups (P-sites). C-sites interact with proteins (such as the bispecific antibodies and BASB) via HA calcium chelation by protein carboxyl clusters. Calcium chelation and coordination are sometimes referred to as calcium affinity. P-sites interact with proteins via phosphoryl cation exchange with positively charged protein amino acid residues (see, e.g., US 2012/0077961). In industrial and commercial settings, HA is most commonly used in the separation of a desired protein from protein production byproducts such as protein aggregates, host-cell proteins and host-cell DNA using phosphate gradients, or, in some circumstances, chloride gradients. However, HA has not been considered for the purification of full length antibodies (e.g., comprising an Fc domain) from Fc containing byproducts because these byproducts would have been believed to elute with the desired product (i.e., the full antibody). For example, the use of sodium chloride in the presence of phosphate was previously believed to cause IgG to bind HA less strongly, resulting in elution not only of the antibody but also the Fc containing contaminants. In contrast, the present inventors have found that an increasing concentration of sodium chloride in the presence of phosphate was surprisingly able to separate a bispecific antibody from one or more BASB.

Various hydroxyapatite chromatography supports are commercially available and are routinely used in the art, any of which can be used in the practice of this invention. These include but are not limited to ceramic hydroxyapatite, hydroxyapatite gels, hydroxyapatite resins and hydroxyapatite powders. Ceramic hydroxyapatite refers to forms of hydroxyapatite in which nanocrystals are aggregated into particles and fused at high temperature to create stable ceramic microspheres suitable for chromatography applications. Commercial examples of ceramic hydroxyapatite include, but are not limited to CHT Type I and CHT Type II (BIORad, USA). The hydroxyapatite microspheres are typically available in particle sizes including, but not limited to, 10, 20, 40, and 80 micron. Hydroxyapatite gel refers to products containing non-ceramic hydroxyapatite embedded in gel supports. A non-limiting example of a hydroxyapatite gel is ULTROGEL™ (Pall Corp., USA), which comprises microfragments of non-ceramic hydroxyapatite embedded in porous agarose microspheres. The selection of the form and/or type of hydroxyapatite, including average particle size, suitable for the methods of the invention is within the ability of the person of ordinary skill in the art, achieved using common knowledge and/or determined by routine experimentation.

The chromatographic methods may be practiced according to any set-up known in the art and/or described herein. Non-limiting examples of chromatographic methods include the use of a packed bed column, a fluidized/expanded bed column and/or a batch operation where the chromatographic medium is mixed with the solution comprising the bispecific antibody. In preferred embodiments, the methods of the invention are practiced using a packed bed column of hydroxyapatite with the column operated in bind-elute mode/conditions.

The methods of the invention separate a bispecific antibody from solutions comprising the bispecific antibody and at least one BASB (i.e., "bispecific antibody solutions"). The methods of the invention are applicable to bispecific antibody solutions that are unpurified or partially purified, and/or filtered or unfiltered. The bispecific antibody solutions may be from natural, synthetic, or recombinant sources. Unpurified bispecific antibody solutions may come from any source known in the art and/or described herein, including, but not limited to, plasma, serum, ascites fluid, milk, plant extracts, bacterial lysates, yeast lysates, cell lysates, recombinant cell lysates and conditioned cell culture media. As used herein, "partially purified solution" may refer to solutions including, but not limited to, bispecific antibody solutions that have been processed by at least one chromatographic process, filtration process, fractionation process, precipitation process, or other standard purification process known in the art, or any combination thereof. The present invention encompasses the combination of the hydroxyapatite chromatographic methods described herein and any other chromatographic process or processes known in the art and/or described herein, including, but not limited to size exclusion, affinity, anion exchange, cation exchange, hydrophobic interaction, immobilized metal affinity chromatography, and mixed-mode chromatography, and combinations thereof.

The hydroxyapatite chromatographic methods as described herein may be combined with one or more affinity chromatographic methods, in particular, using an affinity medium having specificity for an antibody constant domain, for example, including but not limited to an antibody Fc domain and/or an antibody light chain κ- or λ-domain (i.e., includes the use of an Fc-binding agent, a κ-binding agent and/or a λ-binding agent, respectively). Affinity chromatography for the purification of antibodies (e.g., bispecific antibodies) from various solutions based on constant domain-binding agents (e.g., Fc-binding agents) is well known and routinely practiced in the art.

As used herein, the term "Fc-binding agent" and analogous terms refer to a molecule that is capable of binding to the Fc region of an antibody (e.g., an IgG antibody). Non-limiting examples of common Fc-binding agents that may be used according to the methods of the invention include a complement protein, an Fc-receptor, bacterial-derived proteins (such as Protein A and/or Protein G) and combinations thereof. Typically, Fc-binding agents bind antibodies, e.g., IgG, within the $CH_2/CH_3$ region of the heavy chain. In preferred embodiments, the invention is directed to the separation of bispecific antibodies containing an Fc domain/region from a solution comprising the bispecific antibody. In more preferred embodiments, the invention is directed to the separation of bispecific antibodies containing an Fc domain/region from a solution comprising the bispecific antibody and at least one BASB (which necessarily also comprises an Fc domain). Therefore, in certain embodiments, the solution contacted with the hydroxyapatite chromatography medium according to the methods of the invention comprises the pooled bispecific antibody and BASB containing fractions eluted from an affinity column containing an Fc-binding agent.

As used herein, the term "antibody light chain constant domain binding agent" and analogous terms refer to a molecule that is capable of binding to the light chain of an antibody (e.g., an IgG antibody), in particular, to the constant region of the antibody light chain, e.g., to a light chain κ-constant domain/region or a light chain λ-constant domain/region. Non-limiting examples of common antibody light chain constant domain-binding agents that may be used according to the methods of the invention include bacterial-derived proteins (such as Protein L), and single chain antibody fragments having specificity for the light chain (for example, commercially available products such as KappaSelect™ and LambdaFabSelect™ (GE Healthcare, USA)), and combinations of such agents. Typically, Protein L, κ-binding agents and k-binding agents bind antibodies, e.g., IgG, within the constant region of the light chain. In certain embodiments, the invention is directed to the separation of bispecific antibodies containing an antibody light chain constant domain/region from a solution comprising the bispecific antibody. In certain embodiments, the solution contacted with the hydroxyapatite chromatography medium according to the methods of the invention comprises the pooled bispecific antibody containing fractions eluted from an affinity column containing an antibody light chain constant domain-binding agent.

For most commercial purification applications Fc-binding agent and/or antibody light chain constant domain binding agent (e.g., κ-binding agent and/or a λ-binding agent) is immobilized on a solid phase to allow column packing and/or easy separation of the affinity ligand-target molecule (e.g., bispecific antibody and at least one BASB) from the applied solution. The solid phase can comprise, for example but is not limited to, a bead, an agarose matrix, silica, and mixtures thereof.

The hydroxyapatite chromatographic methods according to the invention may be combined with other known processes known in the art and/or described herein for the purification of proteins, peptides and/or polypeptides (e.g., antibodies and bispecific antibodies). Protein/peptide/polypeptide purification processes, in particular, commercial purification processes, commonly employ purification schemes comprising one or more distinct processes/steps/methods such as filtration, precipitation and/or chromatography. The distinct processes/steps/methods may also be referenced as "unit operations" as is known in the art; accordingly, the terms "process", "step", "method" and "unit operation" when used herein in connection with a purification step, e.g., chromatographic method and chromatographic unit operation, are interchangeable. The hydroxyapatite chromatographic methods may be combined with any purification method/unit operation known in the art or described herein including, but not limited to, affinity chromatography using microbial-derived proteins (e.g. protein A, protein G, protein A/G and/or protein L affinity chromatography as noted), ion exchange chromatography (e.g. cation exchange, anion exchange and mixed-mode exchange chromatography), thiophilic adsorption (e.g. with beta-mercaptoethanol and other SH ligands), hydrophobic interaction or aromatic adsorption chromatography (e.g. with butyl-sepharose, phenyl-sepharose, aza-arenophilic resins, or m-aminophenylboronic acid), metal chelate affinity chromatography (e.g. with Ni(II)-, Zn(II) and Cu(II)-affinity material), size exclusion chromatography, and preparative electrophoretic methods (such as gel electrophoresis, capillary electrophoresis) (Vijayalakshmi, M. A., Appl. Biochem. Biotech. 75 (1998) 93-102). Additional non limiting examples of purification steps or unit operations well known in the art include dialysis, hydrophobic interaction chromatography (HIC), hydrophobic charge interaction chromatography (HCIC), ammonium sulphate precipitation, anion or cation exchange chromatography, ethanol precipitation; reverse phase HPLC; chromatography on silica, chromatofocusing and gel filtration. The hydroxyapatite chromatographic methods and/or combination with other purification methods/unit operations as known in the art or described herein are well adapted to separate the bispecific antibody from contaminants and/or impurities, including but not limited to host cell nucleic acids, endotoxin, virus, and other bispecific antibody variants not explicitly encompassed by the term BASB as used herein. An example of a bispecific antibody variant that would be considered a contaminant from the production of the bispecific antibody, but that may not be encompassed by the term BASB as used herein, is a homodimer comprising a pair of heavy chain/light chain polypeptides. Such a homodimer would have a molecular weight and architecture similar to the bispecific antibody (i.e., an architecture similar to a "standard" IgG) but each variable domain would be identical. Such homodimers are referenced herein as ½ antibody homodimers. Accordingly, the hydroxyapatite chromatographic methods according to the invention, whether alone or in combination with one or more purification unit operations as known in the art may separate the bispecific antibody from a solution containing the bispecific antibody and a ½ antibody homodimer, wherein, subsequent to the adsorption of the bispecific antibody or bispecific antibody and ½ antibody homodimer to the hydroxyapatite chromatographic medium, the separation comprises obtaining an eluate fraction comprising the bispecific antibody but not the ½ antibody homodimer. In certain embodiments, the methods of the invention encompass the separation of a bispecific antibody from a solution comprising it and a ½ antibody homodimer, wherein the method comprises a hydroxyapatite chromatographic method as described herein in combination with a cation exchange chromatographic method (which may be upstream or may be downstream of the hydroxyapatite chromatographic method), wherein, subsequent to the hydroxyapatite chromatographic method and cation exchange chromatographic method, the separation comprises obtaining an eluate fraction from either the hydroxyapatite chromatographic method or the cation exchange chromatographic method (depending on the order they are performed) that comprises the bispecific antibody but not the ½ antibody homodimer.

The chromatographic methods disclosed herein are well adapted for use on a commercial scale. The methods may be run in batch or continuous operations, or in a semi-continuous manner, e.g., on a continuous-flow basis of solution containing the desired species, past the chromatographic unit operations, until an entire large batch has thus been filtered (e.g., with one or more optional washing steps interposed between the filtration stages). In this manner, a continuous cycle process can be conducted to give large yields of desired product, in acceptably pure form, over relatively short periods of time.

The bispecific antibody according to the current invention is preferably produced by recombinant means. The routine methods for recombinant production of antibodies are generally adaptable to the production of bispecific antibodies. Such routine methods are well-known in the state of the art and comprise protein expression in prokaryotic or eukaryotic cells (see for example the following reviews: Makrides, S. C., Protein Expr. Purif. 17, 183-202 (1999); Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880). The recombinant production of bispecific antibodies encompasses additional concerns that must be addressed relative to the production of standard antibodies, in particular, relating to the promotion of the hetero-dimerization of two different heavy chains and the promotion of proper heavy chain variable domain-light chain variable domain pairing. However, the successful production of bispecific antibodies, e.g., the promotion of proper polypeptide formation, has become state of the art. For example, the hetero-dimerization of the two different heavy chains has been show to be promoted by the use of "knobs into holes" or "KiH" methodology. In KiH methodology, large amino acid side chains are introduced into the CH3 domain of one heavy chain that fit into appropriately designed cavities in the CH3 domain of the other heavy chain (see, e.g., Ridgeway et al., Protein Eng. 9(1996), 617-621 and Atwell et al., J. Mol. Biol. 270(1997), 677-681). Thus, heterodimers of the heavy chains tend to be more stable than either homodimer, and form a greater proportion of the expressed polypeptides. Further, the association of the desired light-chain/heavy-chain pairs to form the desired Fab domain can be induced by modification of one variable domain (or variable domain-constant region within the Fab domain) of the bispecific antibody (Fab region) to "swap" the constant or constant and variable regions between the light and heavy chains. Thus, in the modified Fab domain, the heavy chain would comprise, for example, $CL-V_H$ or $CL-V_L$ domains and the light chain would comprise $CH_1-V_L$ or $CH_1-V_H$ domains, respectively. This prevents interaction of the light/heavy chain of the modified arm and the light/heavy chain of the standard/non-modified arm. By way of explanation, the heavy chain in the Fab domain of the modified arm, comprising a CL domain, would not interact with the CL domain in the light chain of the standard arm (preventing "improper" pairing of heavy/light chains). This technique for preventing association of improper light/heavy chains is termed "CrossMab" technology and, when combined with KiT technology, results in remarkably enhanced expression of the desired bispecific molecules (see, e.g., Schaefer et al., PNAS 108(2011), 11187-11192). Alternately or additionally, one arm of the antibody may be modified such that the Fab domain is a scFab or scFv, leaving only one "free" light chain in the system. The present invention thus encompasses bispecific antibodies produced by any means known in the art or described herein.

The methods of the present invention are suitable for the separation of any bispecific antibody from a solution comprising it and at least one BASB. The bispecific antibodies according to the disclosed methods may be recombinant immunoglobulins. Further, the bispecific antibodies according to the invention may comprise fragments of humanized immunoglobulins, chimeric immunoglobulins, human immunoglobulins, and/or immunoglobulin conjugates. The bispecific antibodies separated and/or purified by the methods of the current invention may be therapeutic or diagnostic bispecific antibodies. In one embodiment the bispecific antibodies are therapeutic bispecific antibodies. Non-limiting examples of therapeutic bispecific antibodies include a bispecific antibody having specificity for at least one or two of EGFR, HER3, HER4, IGFR, Ep-CAM, CEA, TRAIL, TRAIL-receptor 1, TRAIL-receptor 2, lymphotoxin-beta receptor, CCR4, CD3, CD19, CD20, CD22, CD28, CD33, CD40, CD80, CSF-1R, CTLA-4, death receptor 5 (DR5), IL-17, fibroblast activation protein (FAP), folate receptor 1 (FolR1), hepsin, latent membrane protein 1/2 (LMP 1/2), melanoma-associated chondroitin sulfate proteoglycan (MCSP), prostate-specific membrane antigen (PSMA), VEGF receptor 1, VEGF receptor 2, IGF1-R, TSLP-R, PDGF-R, TIE-I, TIE-2, TNF (TNF-alpha), TNF like weak inducer of apoptosis (TWEAK), IL-IR, VEGF, EGF, PDGF, HGF, angiopoietin 1 and/or 2 (Ang1 and/or Ang2), and a tumor antigen as described herein or known in the art (e.g. growth factor receptors and growth factors).

In preparation for contacting the solution comprising the bispecific antibody and at least one BASB with the hydroxyapatite chromatography medium, it is usually necessary to equilibrate the chemical environment of the medium. This is accomplished by contacting the medium with an equilibration buffer to establish the appropriate pH, conductivity, and concentration of salts to allow for binding of the bispecific antibody to the medium. The equilibration buffer according to the present invention may include phosphate salts at a concentration of about 1 mM to 20 mM, chloride salts at a concentration of about 10 mM to 200 mM, and calcium salts at a concentration of about 0.01 mM to 0.5 mM. In certain embodiments, the equilibration buffer according to the methods of the invention comprises a phosphate salt, a calcium salt and a chloride salt. The equilibration buffer according to the methods of the invention may comprise a phosphate salt at a concentration of about 10 mM, a calcium salt at a concentration of about 0.1 mM and a chloride salt at a concentration of about 50 mM. The equilibration buffer according to the methods of the invention may comprise $NaH_2PO_4$ at a concentration of about 10 mM, $CaCl_2$ at a concentration of about 0.1 mM and NaCl at a concentration of about 50 mM.

The equilibration buffer may also optionally include a buffering compound to confer adequate pH control. Buffering compounds may include but are not limited to IVIES, HEPES, BICINE, imidazole, and Tris. In a non-limiting embodiment, the equilibration buffer according to the methods of the invention may comprise a phosphate salt at a concentration of about 10 mM, a calcium salt at a concentration of about 0.1 mM and a chloride salt at a concentration of about 50 mM in the presence of MES at a concentration of about 20 mM and a pH of about 6.5 to 7.5. In a related or alternate non-limiting embodiment, the equilibration buffer according to the methods of the invention may comprise $NaH_2PO_4$ at a concentration of about 10 mM, $CaCl_2$ at a concentration of about 0.1 mM and NaCl at a concentration of about 50 mM in the presence of MES at a concentration of about 20 mM and a pH of about 6.5 to 7.5.

After equilibration of the hydroxyapatite medium, it may be contacted with the solution comprising the bispecific antibody and at least one BASB. The bispecific antibody and at least one BASB are typically in a solution at conditions that allows their binding to the hydroxyapatite chromatography medium. As is known in the art, such a solution may be termed binding buffer. The binding buffer may have the same or a different composition as the equilibration buffer as defined herein. In certain embodiments, the binding buffer is selected according to the criteria outlined for the equilibration buffer outlined herein. Accordingly, in a non-limiting embodiment, the binding buffer according to the methods of the invention the same as the equilibration buffer. In non-limiting embodiments, the binding-buffer may comprise a phosphate salt at a concentration of about 10 mM, a calcium salt at a concentration of about 0.1 mM and a chloride salt at a concentration of about 50 mM in the presence of MES at a concentration of about 20 mM and a pH of about 6.5 to 7.5. In a related or alternate non-limiting embodiment, the binding buffer according to the methods of the invention may comprise $NaH_2PO_4$ at a concentration of about 10 mM, $CaCl_2$ at a concentration of about 0.1 mM and NaCl at a concentration of about 50 mM in the presence of MES at a concentration of about 20 mM and a pH of about 6.5 to 7.5. In one embodiment comprising a bind and elute chromatographic method, the solution comprising the bispecific antibody and one or more BASB flows through the column containing the hydroxyapatite medium and the bispecific antibody or bispecific antibody and one or more BASB binds to the column (i.e., to the hydroxyapatite medium). The bispecific antibody containing solution may be or may not be followed with a wash buffer, usually of the same composition as the equilibration buffer and/or binding buffer. The wash buffer, if used, may remove one or more contaminants from the column.

Subsequent to the binding of at least the bispecific antibody and optional wash, bispecific antibody is eluted from the hydroxyapatite chromatographic medium under conditions that leave the one or more BASB bound to the medium and/or under conditions wherein the bispecific antibody and the one or more BASB elute separately from the medium. The elution buffer is selected to have a starting composition such that the conductivity value is low. Solutions with low conductivity values suitable for the methods disclosed herein typically have values about or no greater than about 13 mS/cm. Solutions with low conductivity values suitable for the methods disclosed herein may further have conductivity values about or no more than about 10.6 mS/cm, or about or nor more than about 8.5 mS/cm. Non-limiting examples of the starting composition of an elution buffer with a low conductivity value include solutions having a phosphate ion concentration in the range of about 1 mM to about 20 mM, a calcium concentration in the range of about 0.01 mM to about 0.5 mM, and a chloride concentration in the range of about 10 mM to about 200 mM in the presence of a buffering compound (as defined herein in connection with the binding and/or equilibration buffer) at a pH of 6.5 to 8.0. The elution buffer according to the methods of the invention may have a starting composition with a phosphate ion concentration of about 10 mM, a calcium concentration of about 0.1 mM, and a chloride concentration of about 50 mM in the presence of a buffering compound (as defined herein in connection with the binding and/or equilibration buffer) at a pH of about 6.5 to 7.5. In a specific embodiment the elution buffer according to the methods of the invention has a starting composition of 10 mM $NaH_2PO_4$, 0.1 mM $CaCl_2$, and 50 mM NaCl in the presence of 20 mM MES at a pH of 6.5 to 7.5. The methods of the invention elute the bispecific antibody from the hydroxyapatite medium exclusively by increasing the concentration of chloride ions in the elution buffer. The chloride ion concentration may be increased according to a linear gradient, an implemented step gradient (see, e.g., the implemented step gradient of increasing chloride ions represented in FIG. 6), or a combination of these two gradients. The optimization of the gradient to elute the bispecific antibody from the chromatography medium and/or to separate the bispecific antibody from the one or more BASB (i.e., to elute one while the other remains bound to the medium) is within the capability of one of skill in the art in view of the teaching contained herein. The concentration of chloride ions may be increased in the elution buffer by increasing the concentration of one or more chloride salts. Examples of chloride salts that may be added to the elution buffer to increase the concentration of chloride ions include NaCl and KCl. In certain embodiments, the concentration of chloride ions in the elution buffer is increased by increasing the concentration of NaCl. In preferred embodiments, the starting chloride ion concentration of the elution buffer is about 50 mM (which may be provided by one or more chloride salts) and is subsequently increased during the elution to that necessary to elute the bispecific antibody. One of skill in the art may readily determine the maximum concentration of chloride ions necessary for eluting the adsorbed bispecific antibody using routine methods known in the art and according to the teachings and methods described herein. In certain embodiments, the maximum concentration of chloride ions for elution of the bispecific antibody and/or separation of the bispecific antibody from one or more BASB is about 200 mM, about 250 mM, about 300 mM, about 350 mM, about 400 mM or about 500 mM. An exemplary elution buffer according to the methods of the invention has a starting composition of about 10 mM $NaH_2PO_4$, about 50 mM NaCl, about 20 mM MES, and about 0.1 mM $CaCl_2$ at a pH of about 6.5 to 7.5, wherein the concentration of chloride ions is subsequently increased by increasing the concentration of NaCl according to a linear, stepwise or linear-stepwise gradient to about 500 mM during the elution step.

All patents and publications mentioned in this specification are indicative of the levels of those skilled in the art to which the invention pertains. It is to be understood that while certain forms of the invention are illustrated, they are not to be limited to the specific form or arrangement of parts herein described and shown. It will be apparent to those skilled in the art that various changes may be made without departing from the scope of the invention and the invention is not to be considered limited to what is shown and described in the specification. In order that the invention herein described may be more fully understood, the following non-limiting examples are set forth.

EXAMPLES

General Methods
Antibody Expression

Antibodies were transiently expressed in HEK293 cells (Invitrogen). Cell transfection was performed according to the cell supplier's instructions using Maxiprep (Qiagen) preparations of the antibody vectors, Opti-MEM I medium (Invitrogen), 293fectin (Invitrogen), and an initial cell density of $1-2\times10^6$ viable cells/mL in serum-free FreeStyle 293 expression medium (Invitrogen). After 7 days of cultivation in shake flasks or stirred fermenters, antibody containing cell culture supernatants were harvested by centrifugation and filtered through a sterile filter (0.22 µm). Supernatants were processed immediately after harvesting or were stored at −80° C. until purification.

Protein A Affinity Chromatography

Molecules containing Fc regions/domain were purified from the sterile filtered culture supernatants by affinity chromatography using a Protein A—Sepharose column (MabSelectSure-Sepharose™ (GE Healthcare, Sweden)). Briefly, culture supernatants were first applied to the Protein A column equilibrated with PBS buffer (10 mM $Na_2HPO_4$, 1 mM $KH_2PO_4$, 137 mM NaCl and 2.7 mM KCl, pH 7.4). The column was subsequently washed with equilibration buffer and the antibodies eluted with 25 mM sodium citrate, pH 3.0. The antibody fractions were pooled and prepared for hydroxyapatite chromatography by buffer exchange to 10 mM $NaH_2PO_4$, 50 mM NaCl, 20 mM MES, 0.1 mM $CaCl_2$, pH 6.5-7.5 using a desalting column or by extensive dialysis.

Hydroxyapatite Chromatography

Hydroxyapatite chromatography was performed using MacroPrep CHT type II hydroxyapatite resin (BioRad, USA). Following equilibration of the hydroxyapatite resin with 10 mM $NaH_2PO_4$, 50 mM NaCl, 20 mM MES, 0.1 mM $CaCl_2$, pH 6.5-7.5, the antibody load fluid prepared as described above was applied to the column. The column was then washed with equilibration buffer and the bound material eluted in a linear gradient or a linear gradient with implemented steps to 10 mM $NaH_2PO_4$, 500 mM NaCl, 20 mM MES, 0.1 mM $CaCl_2$, pH 6.5-7.5. Protein concentration in the eluate (eluted fractions) was monitored by absorbance at 280 nm (presented as chromatograms as indicated herein).

CE-SDS Analysis

Both prior to and after hydroxyapatite chromatography, load and/or fraction composition, including determination of percentage of bispecific antibody, bispecific antibody fragments and/or bispecific antibody specific byproduct (including estimated molecular weights) was analyzed by sodium dodecyl sulfate capillary electrophoresis (CE-SDS). CE-SDS was performed according to the manufacturer's instructions using microfluidic Labchip technology (PerkinElmer, USA). Briefly, 5 µl of load fluid (pre-hydroxyapatite chromatography; that is the eluate (i.e., antibodies) eluted from the Protein A affinity column) and eluate from the hydroxyapatite column were prepared for CE-SDS analysis using the HT Protein Express Reagent Kit according manufacturer's instructions and analyzed on LabChip GXII system using a HT Protein Express Chip. Data were analyzed using LabChip GX Software.

Example 1: Separation of ½ Antibody Fragment and Bispecific CrossMab EGFR-IGFR

Methods

An anti-EGFR/anti-IGFR bispecific antibody was designed according to CrossMab and knob in hole (KiH) method described, e.g., in Schaefer et al., *PNAS USA* 108(2011), 11187-11192. The bispecific antibody was expressed, purified from culture supernatant using Protein A affinity chromatography, and analyzed with CE-SDS as described above in General Methods.

Subsequent to the Protein A affinity purification, the antibody containing solution was loaded onto a hydroxyapatite column and eluted in a linear salt gradient as described above.

Results

The antibody containing fractions eluted from the Protein A column were pooled to form the load fluid for hydroxyapatite chromatography and analyzed for protein composition. CE-SDS analysis revealed that the load fluid contained two predominant protein species. Approximately 43% of the total protein was a protein having an approximate molecular weight of 94 kD and approximately 33% was a protein having an approximate molecular weight of 160 kD; the two protein species were identified as a ½ antibody fragment (i.e., a fragment of the bispecific antibody containing a single heavy chain and a single light chain) and the "complete" bispecific antibody, respectively (FIG. 1).

Figure 2:
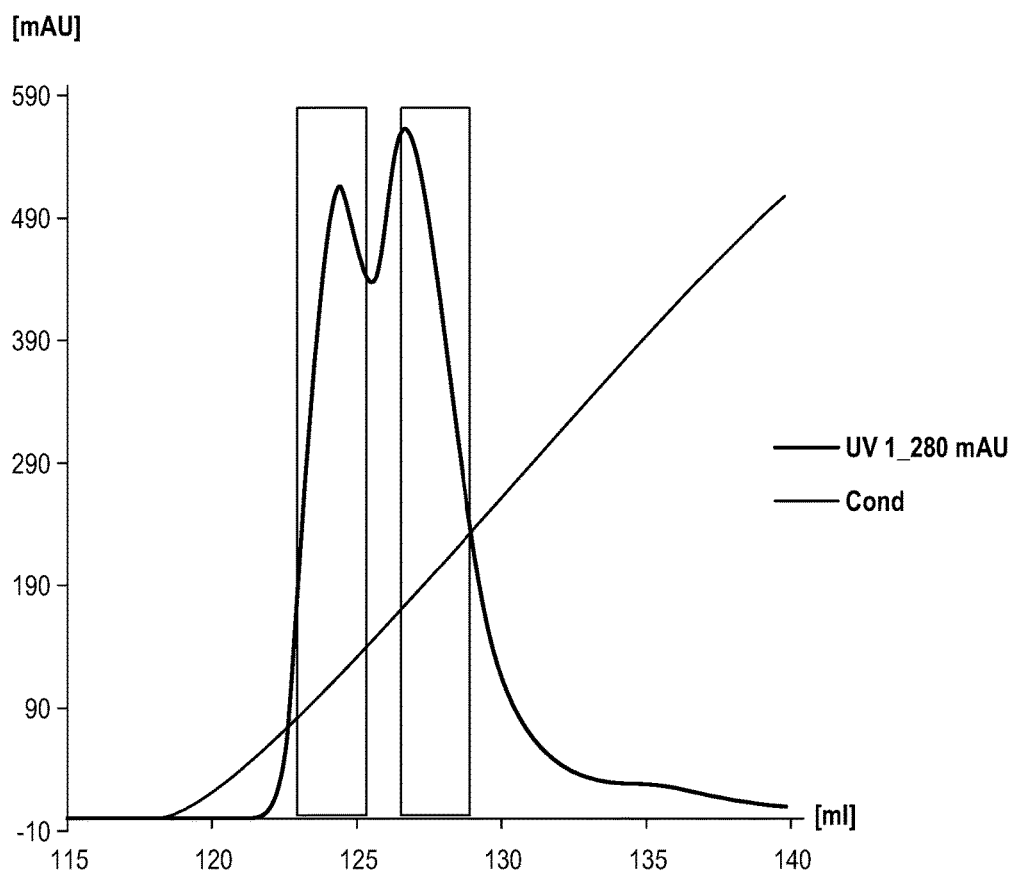
FIG. 2 Elution profile from the hydroxyapatite chromatography column (monitored by UV absorption at 280 nm) of the bispecific antibody composition analyzed in FIG. 1. Elution was achieved with an increasing gradient (linear gradient) of NaCl in the elution buffer represented by the sloped line.
Figure 3:
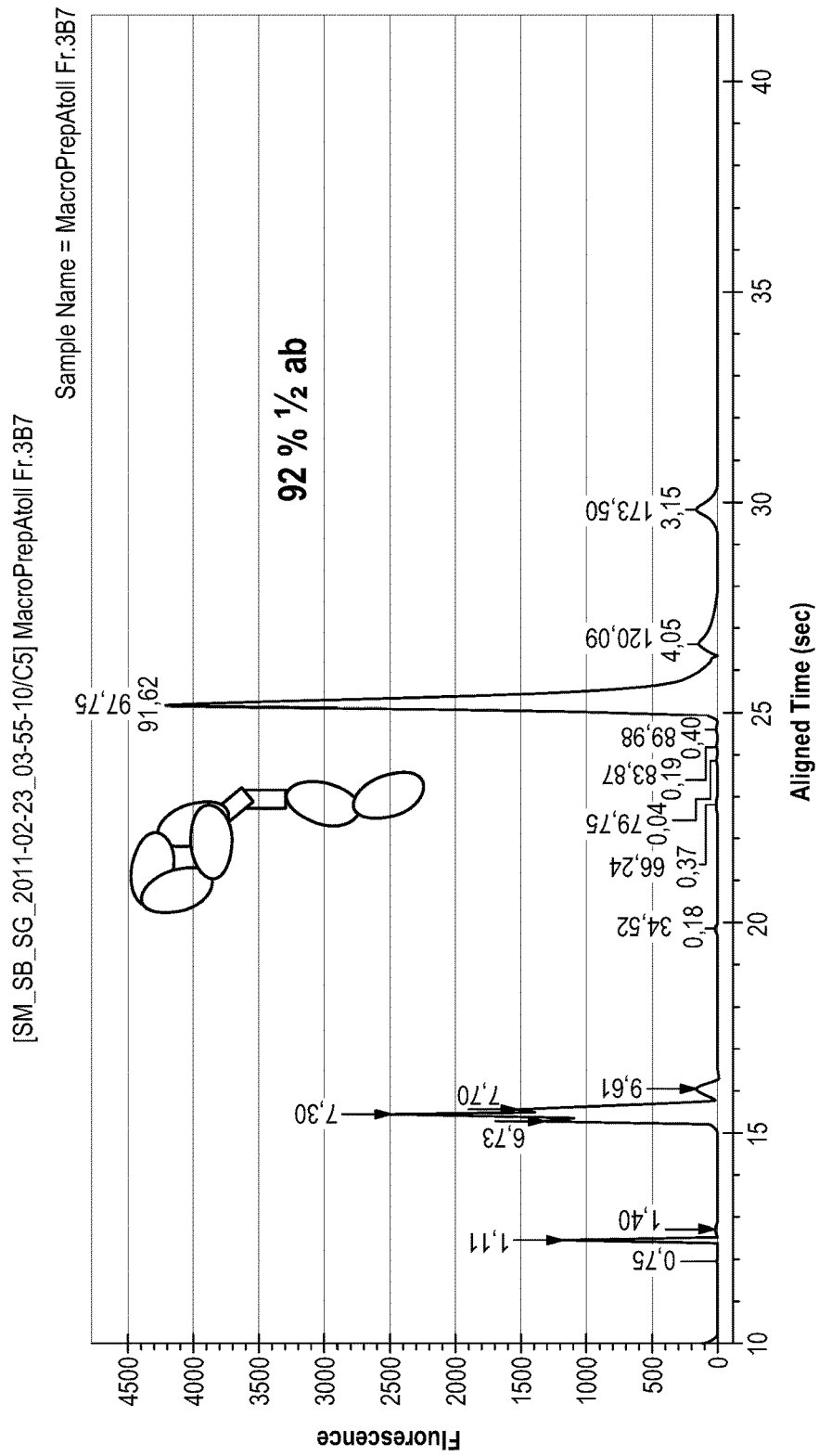
FIG. 3 Non-reducing CE-SDS analysis of first elution peak from FIG. 2 (left gray box).
Figure 4:
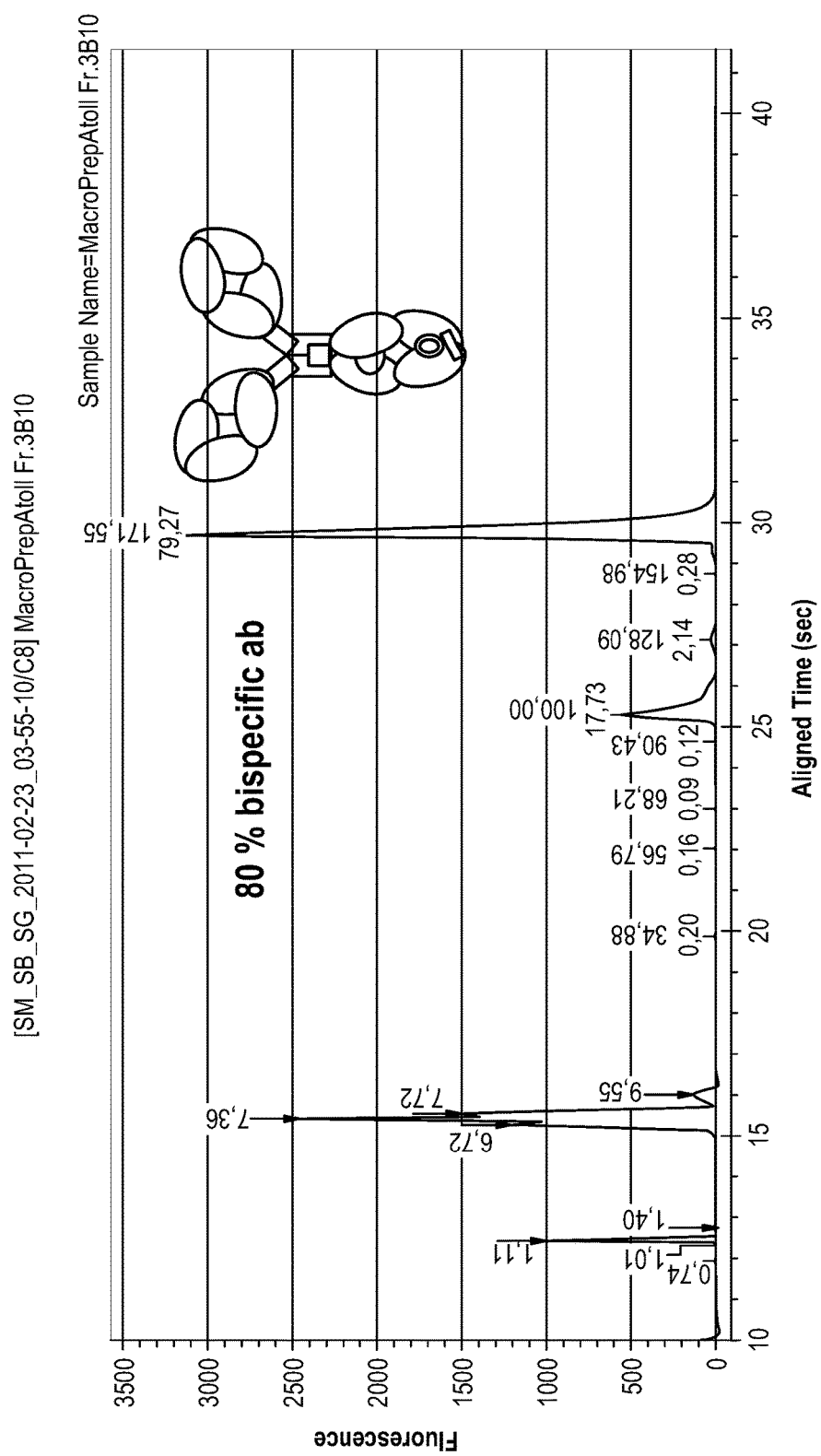
FIG. 4 Non-reducing CE-SDS analysis of second elution peak from FIG. 2 (right gray box).

The load fluid was applied to the hydroxyapatite column and eluted with a linear salt gradient as described above and as represented by the sloped line in FIG. 2. FIG. 2 also shows the elution profile from the hydroxyapatite column as monitored by UV absorption at 280 nm. The ½ antibody species eluted from the hydroxyapatite column at a lower salt concentration and with almost no coelution of the desired bispecific antibody: approximately 92% of the total protein in pooled fractions represented by the left gray box of FIG. 2 was found to be the ½ antibody byproduct/contaminant, with less than 4% being bispecific antibody (determined by CE-SDS, FIG. 3). The bispecific antibody eluted as a second peak: approximately 80% of the protein in pooled fractions represented by the right gray box of FIG. 2 was found to be the bispecific antibody (determined by CE-SDS, FIG. 4).

The results demonstrate that the methods of the invention allow the ready separation of bispecific antibody from at least ½ antibody byproduct/contaminant.

Example 2: Separation of ½ Antibody Fragment and Bispecific scFab Ang2-VEGF

Methods

Example 2 follows the methodology of Example 1 with the following exceptions: the bispecific antibody was an anti-Ang2/anti-VEGF bispecific antibody designed using the KiH method, but not the CrossMab method. Instead, the Ang2 specific variable domain was designed as a scFab, which prevented improper pairing of the various light and heavy chain variable domains as described herein, e.g., in the background section. Further, subsequent to the Protein A capture, the antibody containing solution was eluted from the hydroxyapatite column using a linear salt gradient with an implemented step.

Results

Figure 5:
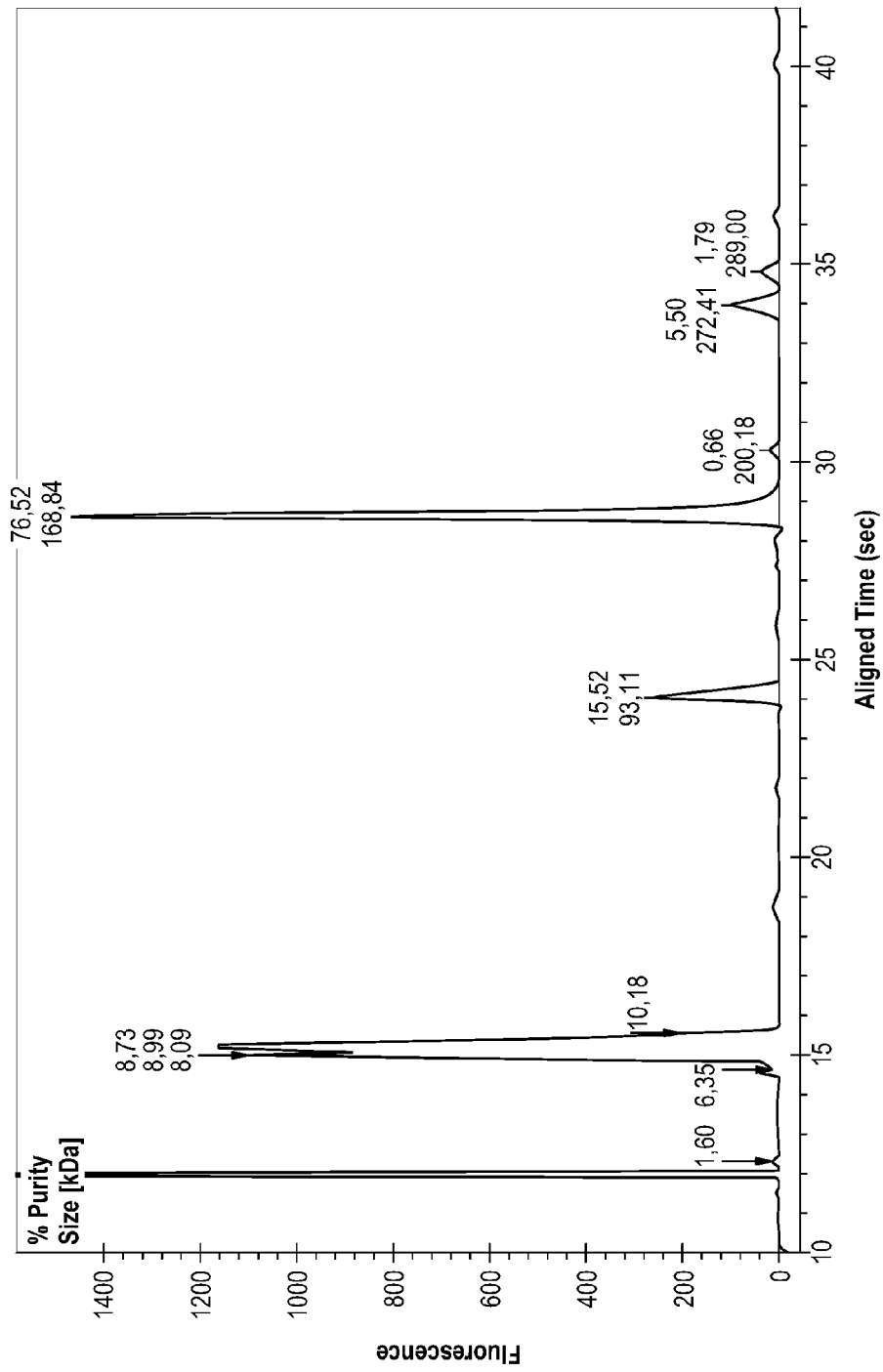
FIG. 5 Non-reducing CE-SDS analysis of production culture supernatant of KiH/scFab bispecific antibody, anti-VEGF/anti-Ang2, subsequent to Protein A chromatography.

CE-SDS analysis of the pooled antibody containing fractions from Protein A affinity chromatography revealed that the load fluid prior to hydroxyapatite chromatography contained three predominant protein species: approximately 16% was a ½ antibody fragment, approximately 77% was the desired bispecific antibody, and approximately 6% was higher molecular weight aggregates (FIG. 5).

Figure 6:
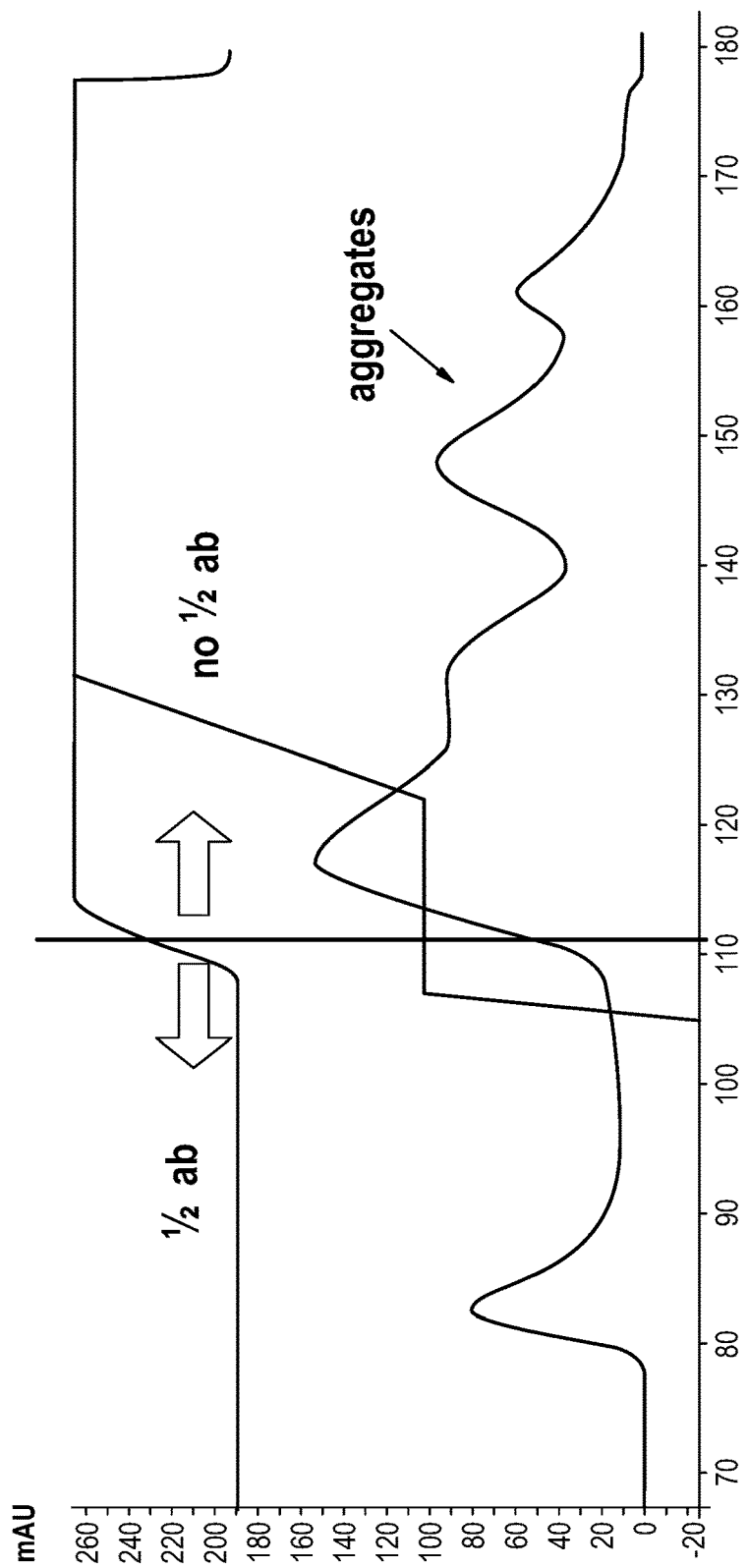
FIG. 6 Elution profile from the hydroxyapatite chromatography column (monitored by UV absorption at 280 nm) of the bispecific antibody composition analyzed in FIG. 5. Elution was achieved with an increasing gradient (linear gradient with implemented step) of NaCl in the elution buffer represented by the sloped and stepped line.
Figure 7:
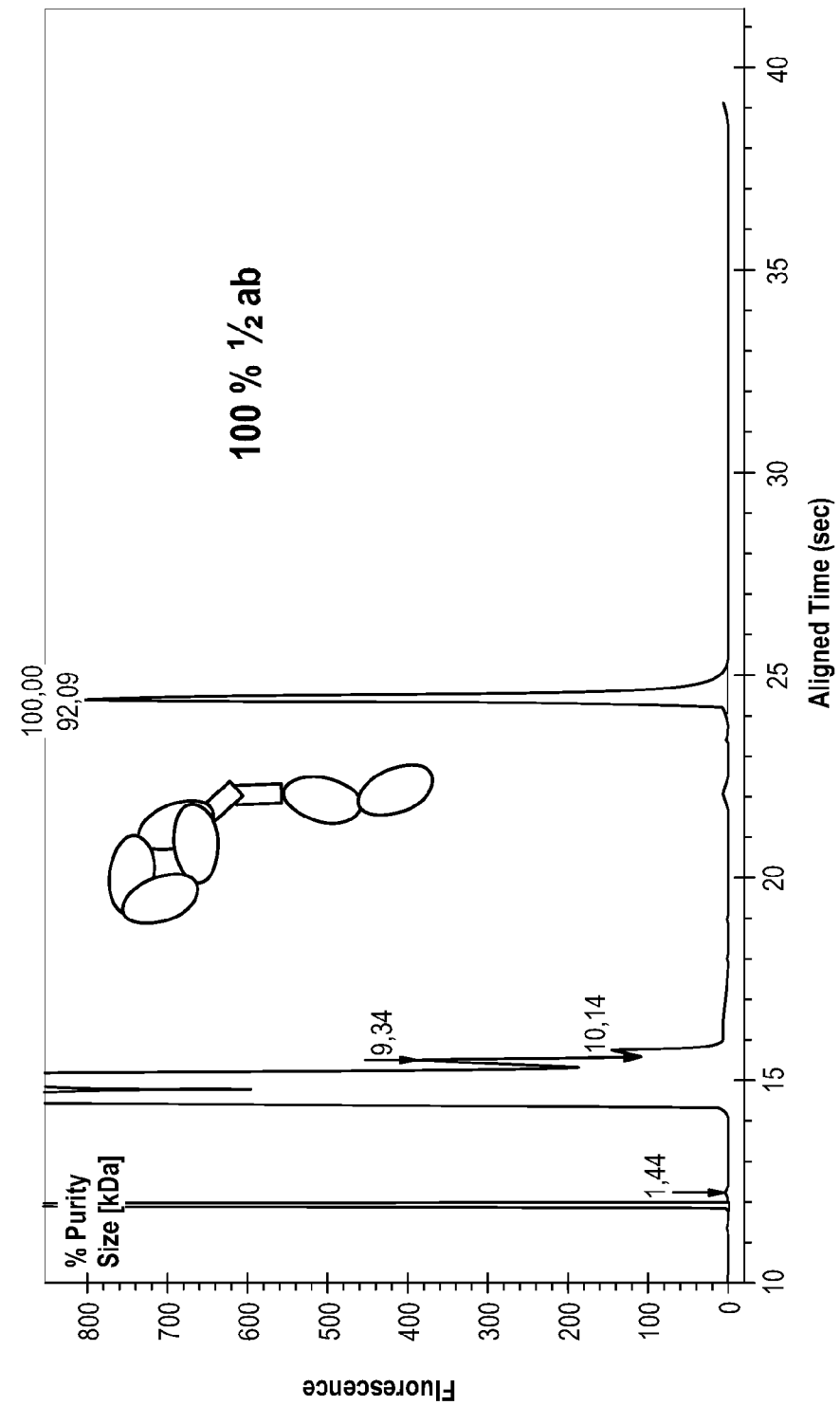
FIG. 7 Non-reducing CE-SDS analysis of first elution peak and pooled fractions from left of vertical black line in FIG. 6.
Figure 8:
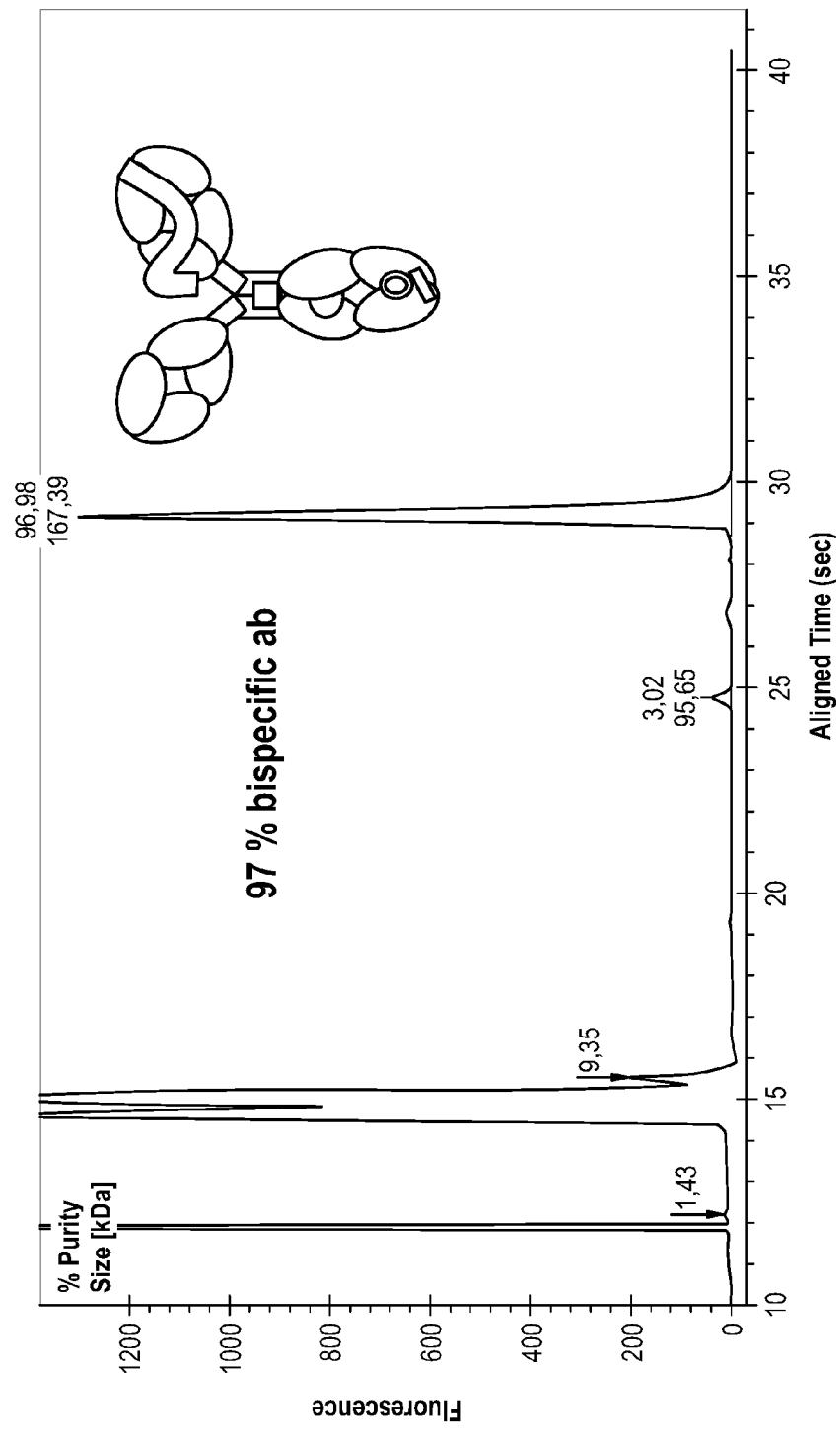
FIG. 8 Non-reducing CE-SDS analysis of second elution peak from FIG. 6 (first elution peak to right of vertical black line in FIG. 6.

The load fluid was applied to the hydroxyapatite column and eluted with a linear salt gradient with implemented step represented by the stepped and sloped line in FIG. 6. FIG. 6 also shows the elution profile from the hydroxyapatite column as monitored by UV abruption at 280 nm. The ½ antibody species eluted at a significantly lower salt concentration than the bispecific antibody and could be entirely separated from "complete" bispecific species and larger aggregates. 100% of the protein species eluting at the low salt concentration was revealed to be the ½ antibody fragment (FIG. 7: analysis of pooled fractions to the left of the bold vertical line of FIG. 6) Bispecific antibody and antibody aggregates then eluted separately as salt concentration increased. Pooled fractions containing the bispecific antibody (representing the first peak to the right of the solid black line in FIG. 6) were revealed to be approximately 97% pure bispecific antibody (FIG. 8).

The results demonstrate that the methods of the invention allow the ready separation of bispecific antibody from at least ½ antibody byproduct/contaminant as well as antibody aggregates, including 5/4 antibody byproducts/contaminants.

Example 3: Separation of ¾ Antibody Fragment and Bispecific CrossMab Ang2-VEGF Methods Example 2 was repeated, but with the bispecific Ang2-VEGF antibody designed according to CrossMab methodology. Again, subsequent to the Protein A capture, the antibody containing solution was eluted from the hydroxyapatite column using a linear salt gradient.

Results

CE-SDS analysis of the pooled antibody containing fractions from Protein A affinity chromatography revealed that the load fluid prior to hydroxyapatite chromatography contained approximately 7.8% of a ¾ antibody fragment (i.e., the bispecific antibody lacking one light chain) and 85% bispecific antibody (data not shown).

Figure 9:
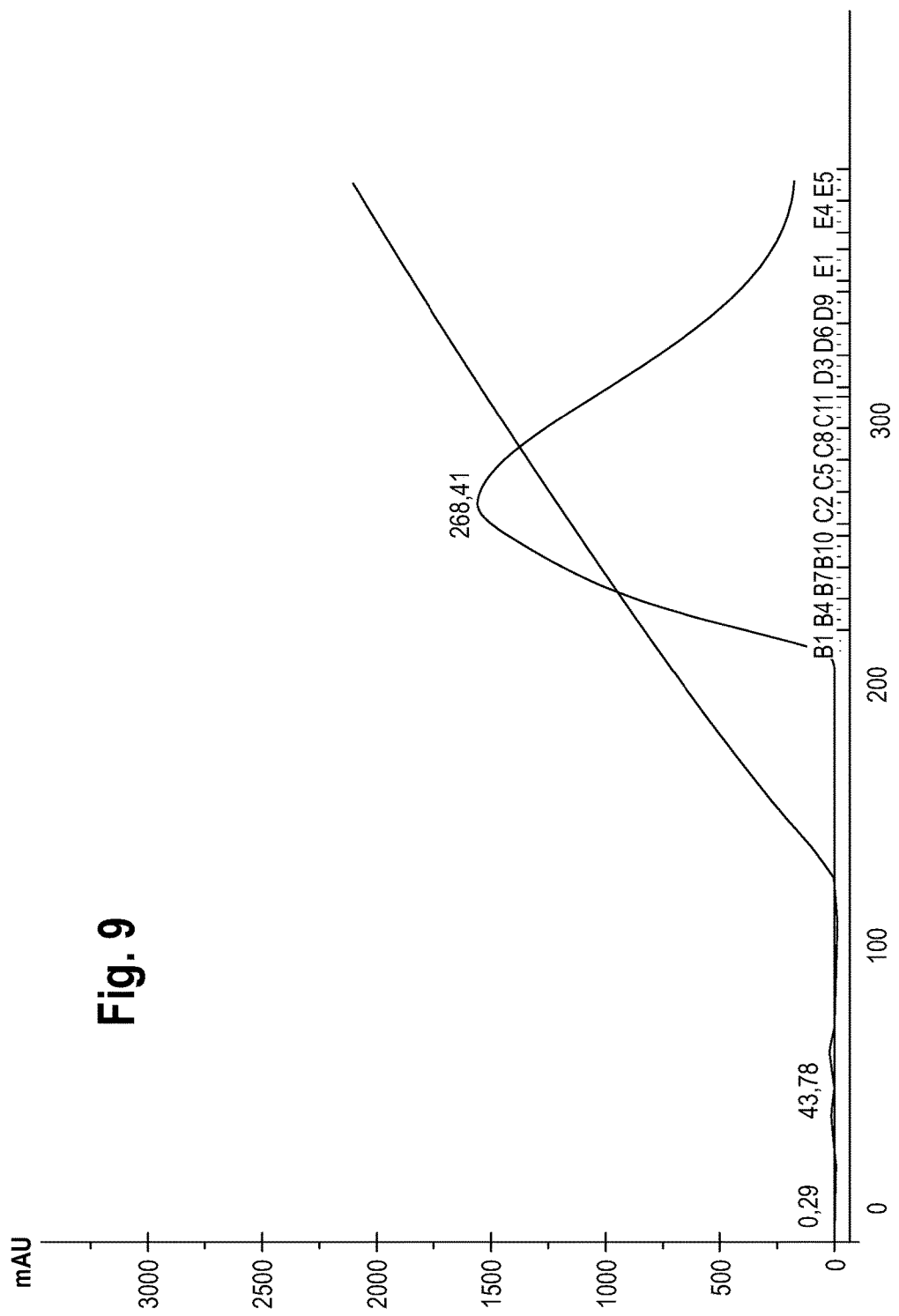
FIG. 9 Elution profile from the hydroxyapatite chromatography column (monitored by UV absorption at 280 nm) of a production culture supernatant of a KiH/CrossMab bispecific antibody, anti-VEGF/anti-Ang2 that was subjected to protein A chromatography prior to loading on the hydroxyapatite column. Elution was achieved with an increasing gradient (linear gradient) of NaCl in the elution buffer represented by the sloped line.

The load fluid was applied to the hydroxyapatite column and eluted with a linear salt gradient represented by the sloped line in FIG. 9. The ¾ antibody was enriched in the side fractions of the peak in FIG. 9. For example, fraction C4 (FIG. 9) contained 95% bispecific antibody and 1.8% ¾ antibody; fraction D8 contained 78% bispecific antibody and 9.1% ¾ antibody. Thus, the results demonstrate that the methods of the invention allow the substantial separation of bispecific antibody from at least the ¾ antibody byproduct/contaminant.

Example 4: Separation of ½ Antibody Fragment and Bispecific scFab EGFR-IGFR

Methods

Example 4 follows the methodology of Example 2 with the following exceptions: the bispecific antibody was an anti-EGFR/anti-IGFR bispecific antibody. As with Example 2, the bispecific antibody was designed using KiH but not CrossMab methodology, with the IGFR antigen binding domain being a scFab. The antibody containing fractions were eluted from the hydroxyapatite column using a linear salt gradient with an implemented step.

Results

Figure 10:
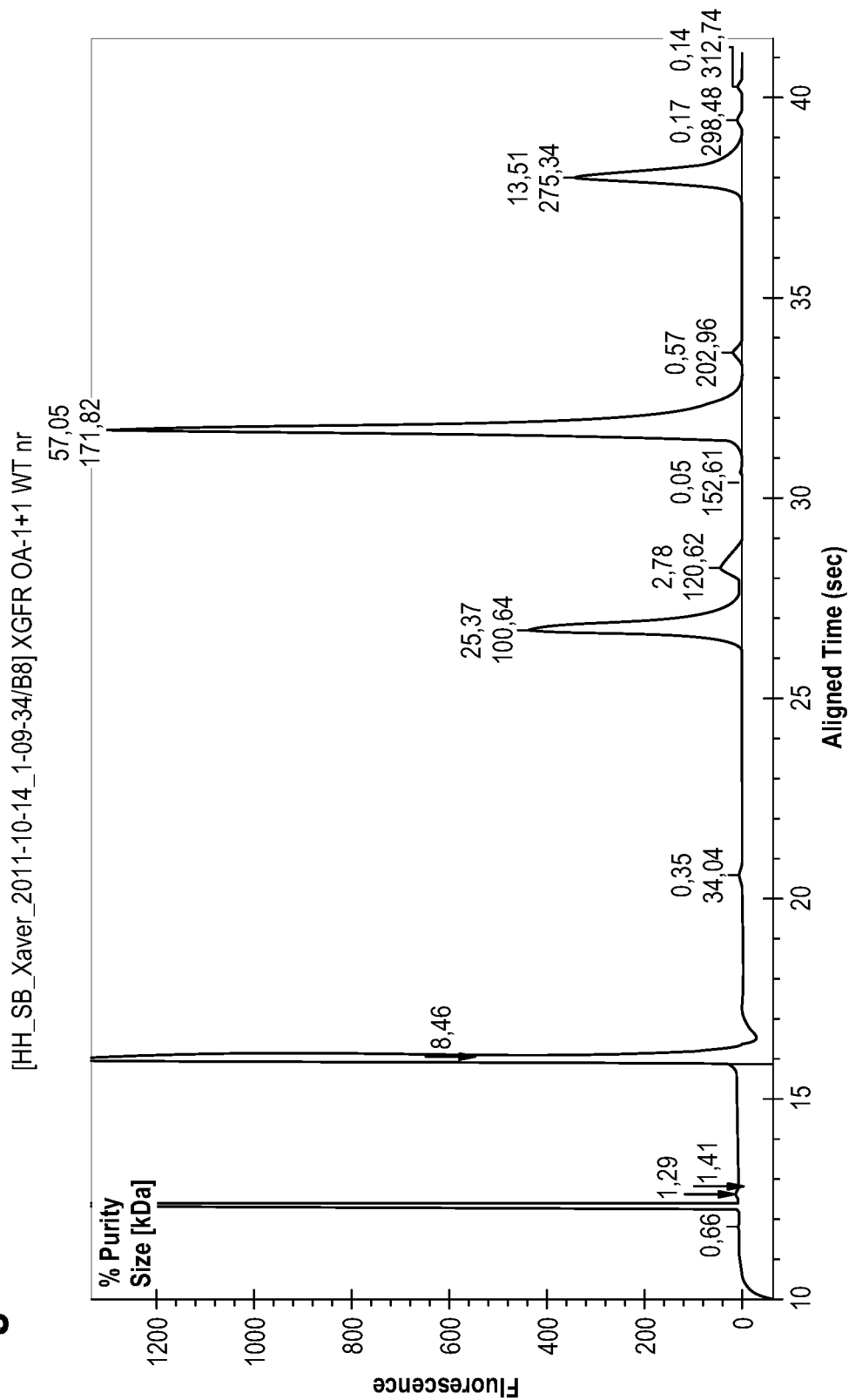
FIG. 10 Non-reducing CE-SDS analysis of production culture supernatant of KiH/scFab bispecific antibody, anti-EGFR/anti-IGFR, subsequent to Protein A chromatography.

CE-SDS analysis of the pooled antibody containing fractions from Protein A affinity chromatography revealed that the load fluid prior to hydroxyapatite chromatography contained three predominant protein species, parallel with that observed for example 2: approximately 25% was a ½ antibody fragment, approximately 57% was the desired bispecific antibody and about 14% was higher molecular weight aggregates (FIG. 10).

Figure 11:
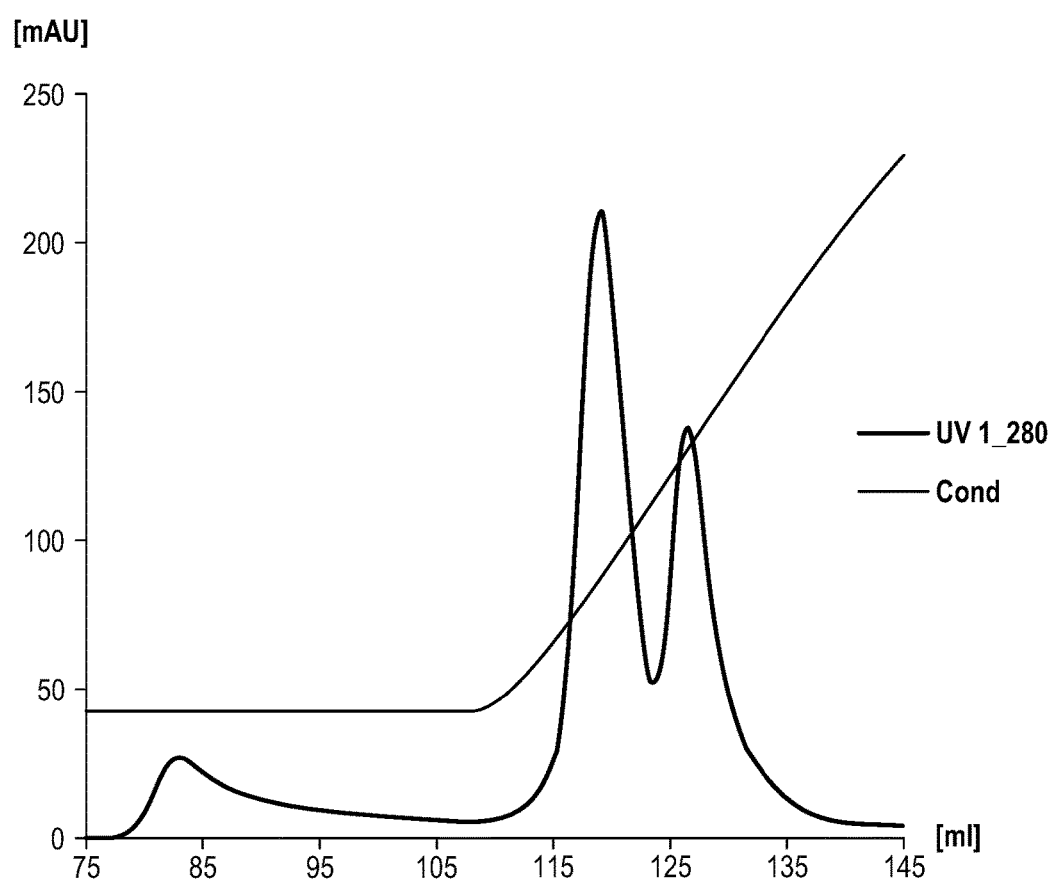
FIG. 11 Elution profile from the hydroxyapatite chromatography column (monitored by UV absorption at 280 nm) of the bispecific antibody composition analyzed in FIG. 10. Elution was achieved with an increasing gradient (linear gradient with implemented step) of NaCl in the elution buffer represented by the sloped and stepped line.
Figure 12:
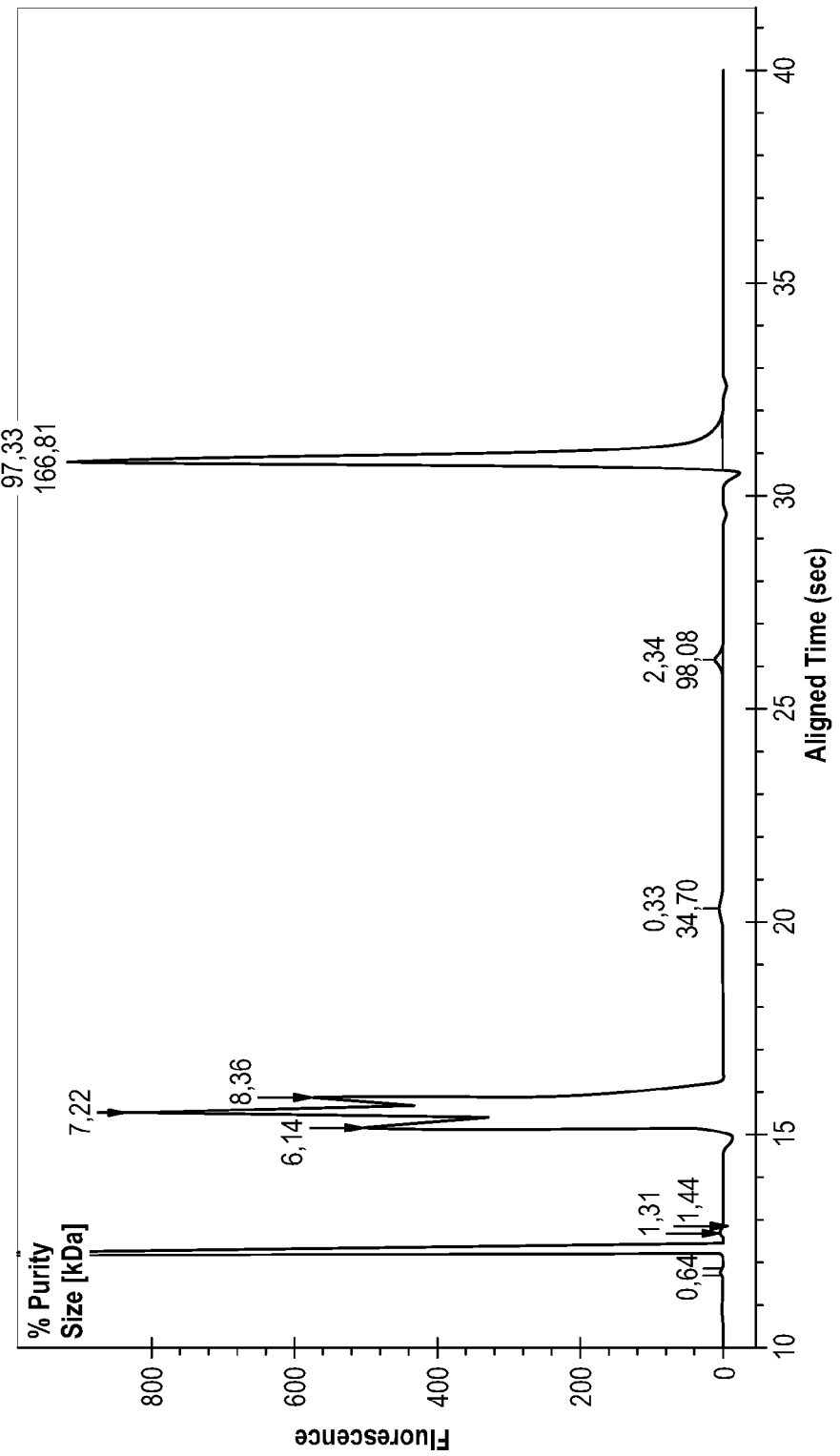
FIG. 12 Non-reducing CE-SDS analysis of second elution peak from FIG. 11.

The load fluid was applied to the hydroxyapatite column and eluted with a linear salt gradient with implemented step represented by the stepped and sloped line in FIG. 11. The ½ antibody species eluted at a low salt concentration with the bispecific antibody and antibody aggregates separately eluting at progressively higher concentrations (FIG. 11). Pooled fractions from the elution peak of the bispecific antibody were determined to contain approximately 97% bispecific antibody, with little contamination from the ½ antibody fragment/byproduct or aggregates (FIG. 12). Thus, the linear and stepped salt gradient allowed the ready separation and purification of the bispecific antibody from both the ½ antibody fragment/byproduct and the antibody aggregates.

Example 5: Separation of 5/4 Antibody and Bispecific scFab TWEAK-IL17

Methods

Example 5 follows the methodology of Examples 2 and 3 with the following exceptions: the bispecific antibody was an anti-TWEAK/anti-IL17 bispecific antibody. As with Examples 2 and 3, the bispecific antibody was designed using KiH but not CrossMab methodology, with the TWEAK antigen binding domain being a scFab. The antibody containing fractions were eluted from the hydroxyapatite column using a linear salt gradient with an implemented step.

Results

Figure 13:
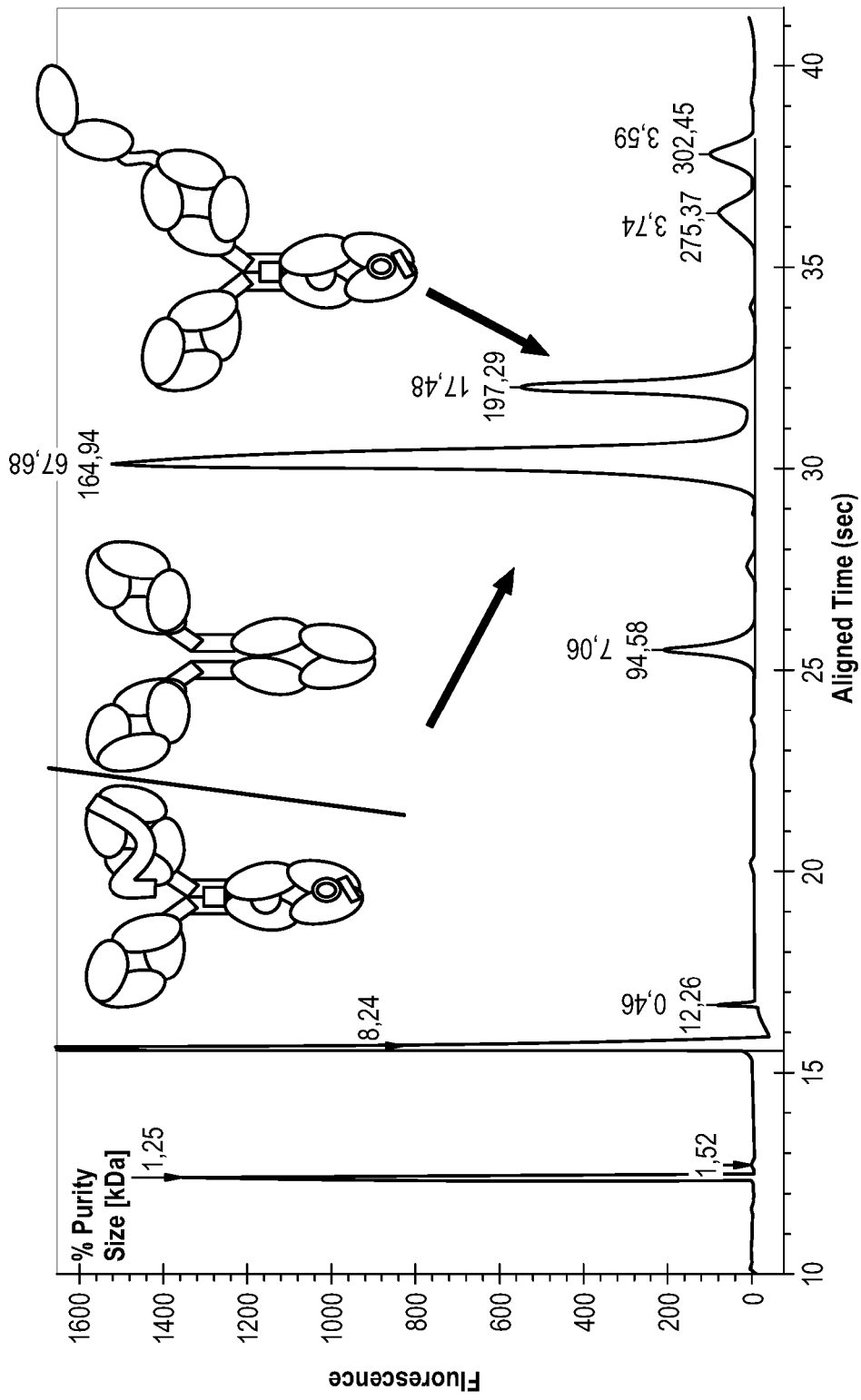
FIG. 13 Non-reducing CE-SDS analysis of production culture supernatant of KiH/scFab bispecific antibody, anti-IL17/anti-TWEAK, subsequent to Protein A chromatography.

CE-SDS analysis of the pooled antibody containing fractions from Protein A affinity chromatography revealed that the load fluid prior to hydroxyapatite chromatography contained two predominant protein fractions: approximately 17% was a 5/4 antibody species (likely containing an extra IL17 light chain) while approximately 68% was a faction having the apparent molecular weight of the desired bispecific antibody (FIG. 13). Subsequent analysis revealed that the fraction containing the protein having the apparent molecular weight of the bispecific protein was a mixture of the bispecific protein and a homodimer of anti-IL17 heavy chain/light chain pairs, i.e., equivalent to a monospecific or "standard" anti-IL17 antibody (data not shown; confirmed by CE-SDS performed under reducing conditions).

Figure 14:
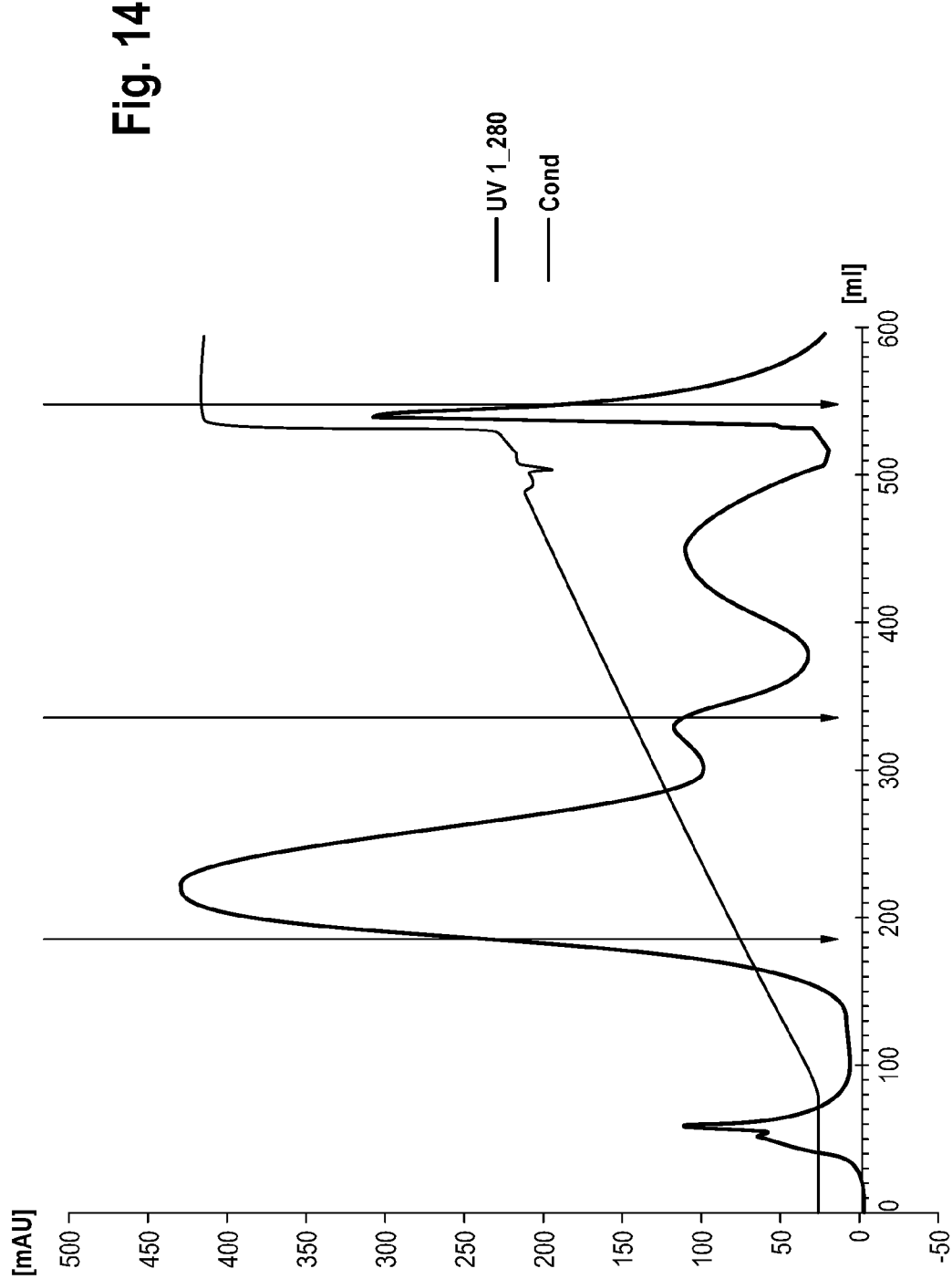
FIG. 14 Elution profile from the hydroxyapatite chromatography column (monitored by UV absorption at 280 nm) of the bispecific antibody composition analyzed in FIG. 13. Elution was achieved with an increasing gradient (linear gradient with implemented step) of NaCl in the elution buffer represented by the sloped and stepped line. The Black arrows within the first, second and third elution peaks indicates the fractions that were subsequently analyzed by CE-SDS (presented in FIGS. 15 and 16; analysis of fraction indicated by third arrow not shown).
Figure 15:
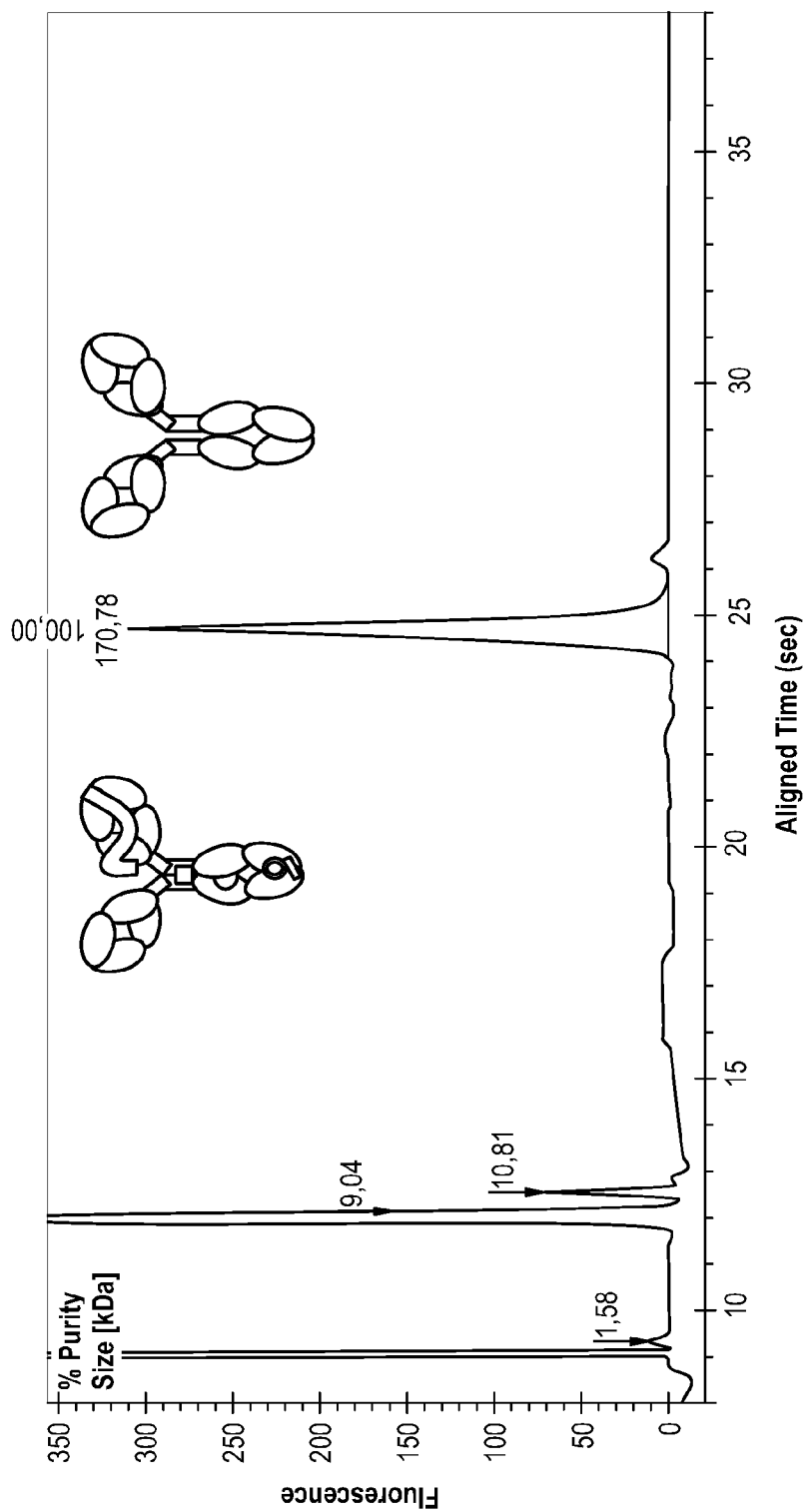
FIG. 15 Non-reducing CE-SDS analysis of first elution peak from FIG. 14 (first/leftmost black arrow).
Figure 16:
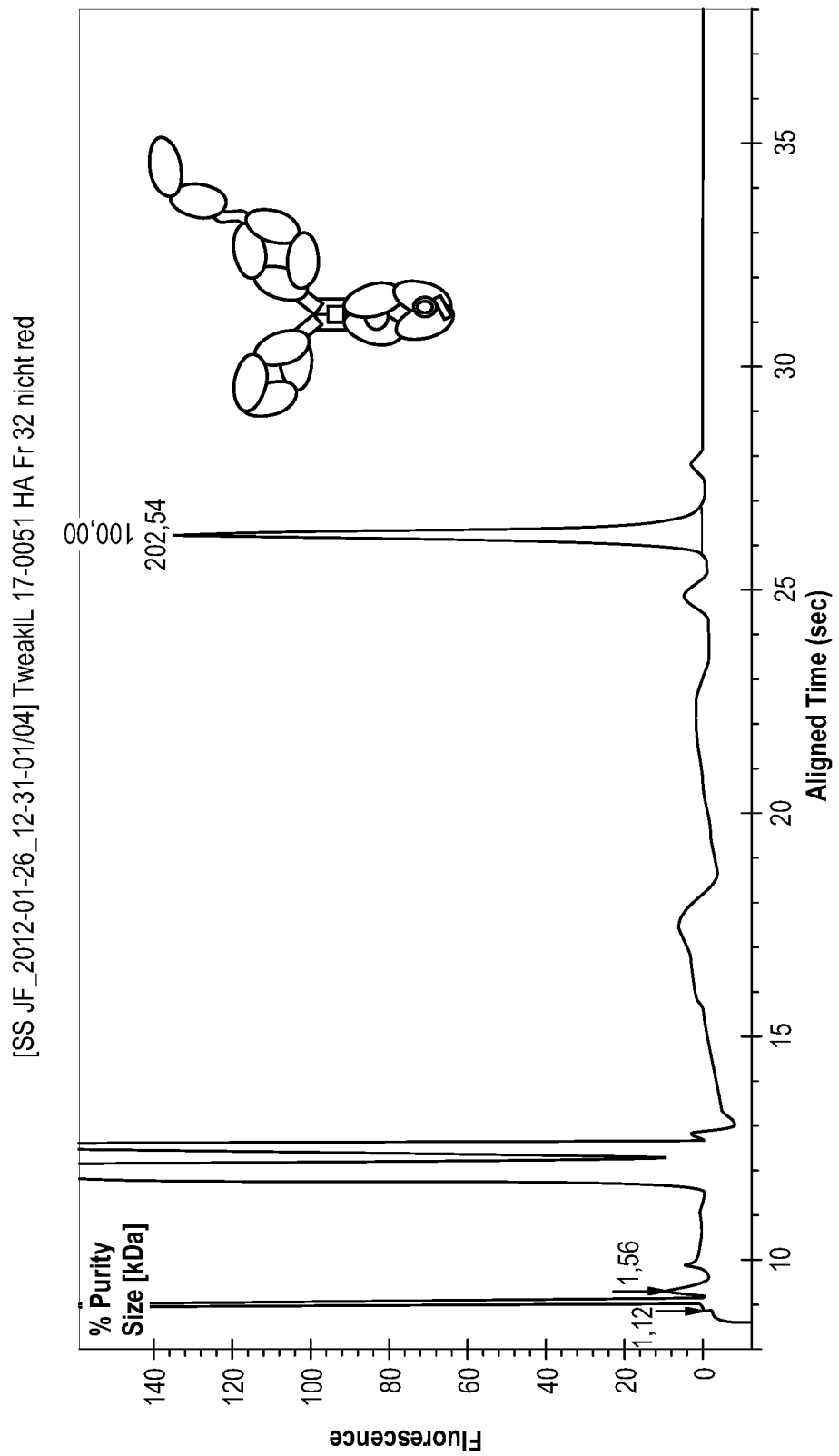
FIG. 16 Non-reducing CE-SDS analysis of second elution peak from FIG. 14 (second/middle black arrow).

The load fluid was applied to the hydroxyapatite column and eluted with a linear salt gradient with implemented step represented by the sloped and stepped line in FIG. 14. The bispecific antibody and homodimer co-eluted in a single peak at a lower salt concentration (see, first peak, FIG. 14 and FIG. 15). The 5/4 antibody eluted separately at higher salt concentration (see, $3^{rd}$ peak in FIG. 14; $4^{th}$ peak is protein aggregates). Pooled fractions from the first elution peak were determined to contain only bispecific antibody and homodimer, with no observable contamination from higher molecular weight species, e.g., 5/4 antibody (FIG. 15). Similarly, pooled fractions of the eluation peak relating to the 5/4 antibody, revealed that this specifies eluted with no detectable contamination from the bispecific antibody or homodimer (FIG. 16). Thus, the linear and stepped salt gradient allowed the ready separation and purification of the bispecific antibody from at least 5/4 antibodies and/or byproducts having only minimally greater molecular weights as the molecule of interest.

Example 6: Separation of Homodimer and Bispecific scFab TWEAK-IL17

Methods

Example 5 demonstrated that hydroxyapatite chromatography according to the methods of the invention was able to separate bispecific antibody from 5/4 antibody contaminants; however, the bispecific antibody co-eluted with a homodimer of paired anti-IL17 heavy/light chains (i.e., equivalent to a "standard" or monospecific anti-IL17 antibody). The separation of the homodimer and bispecific antibody was investigated using PorosHS50 cation exchange chromatography using a linear salt gradient.

Results

Figure 17:
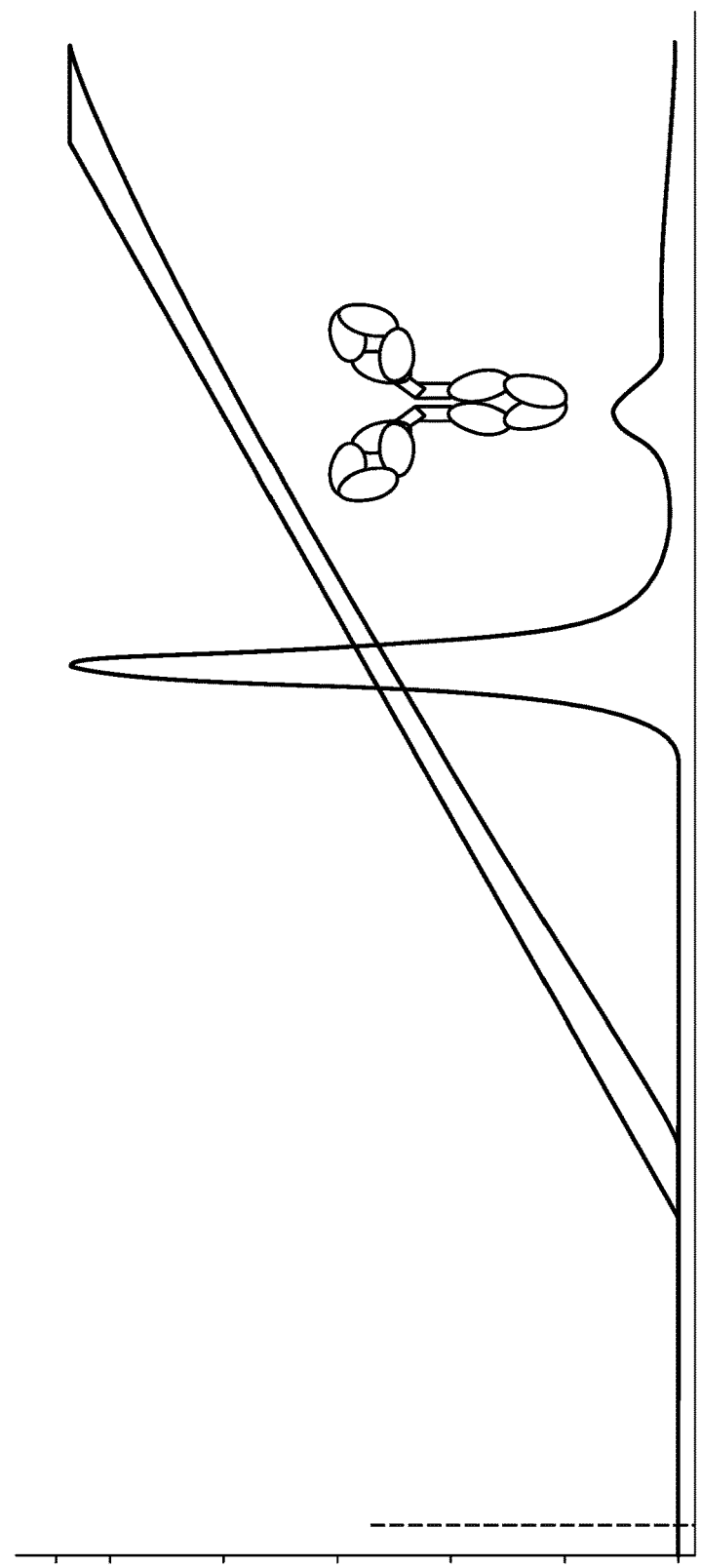
FIG. 17 Elution profile from cation exchange chromatography column (monitored by UV absorption at 280 nm) of the bispecific antibody composition analyzed in FIG. 13. Elution was achieved with an increasing gradient (linear gradient) of NaCl in the elution buffer represented by the sloped line.
Figure 18:
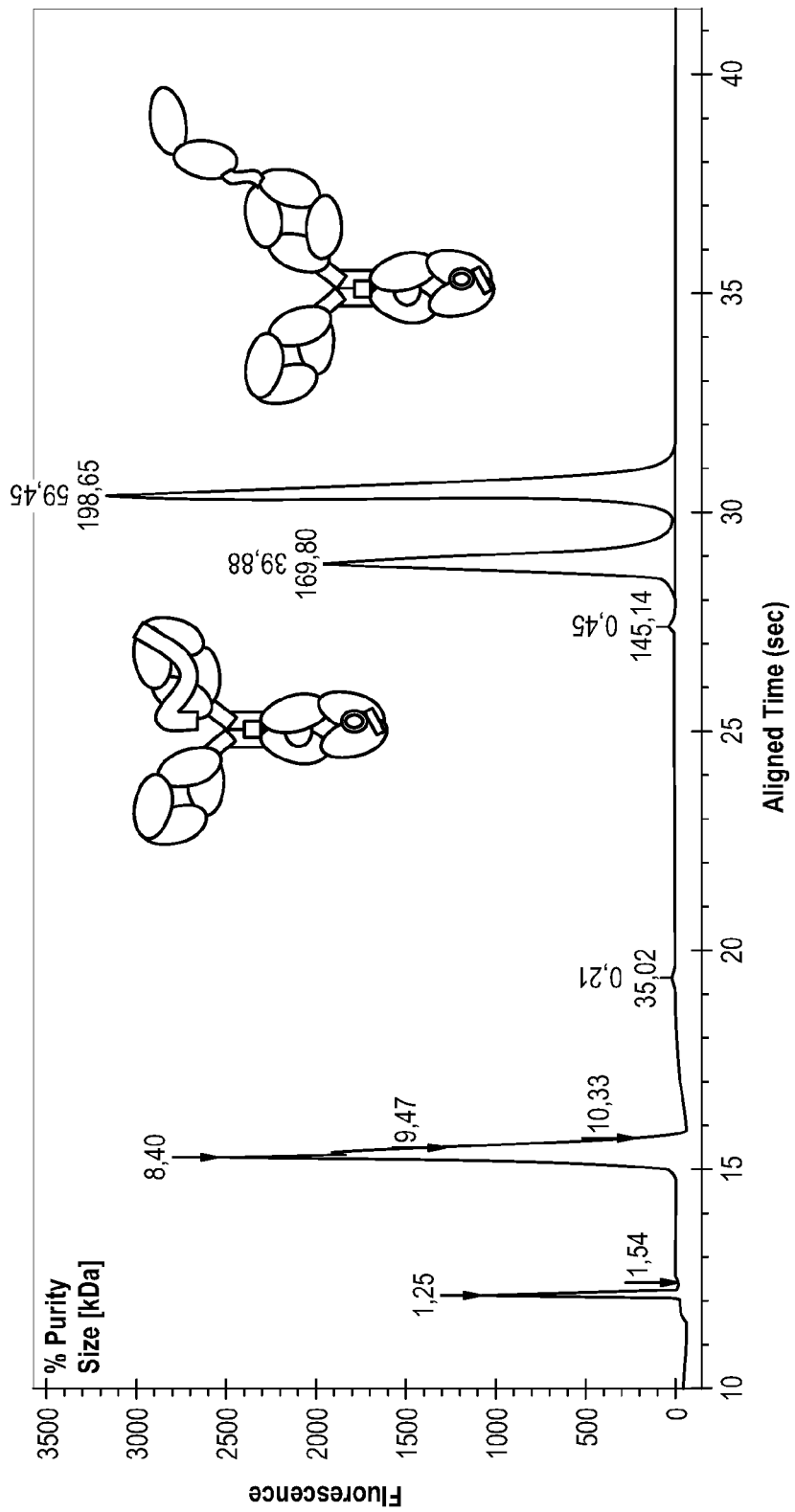
FIG. 18 Non-reducing CE-SDS analysis of first elution peak from FIG. 17.
Figure 19:
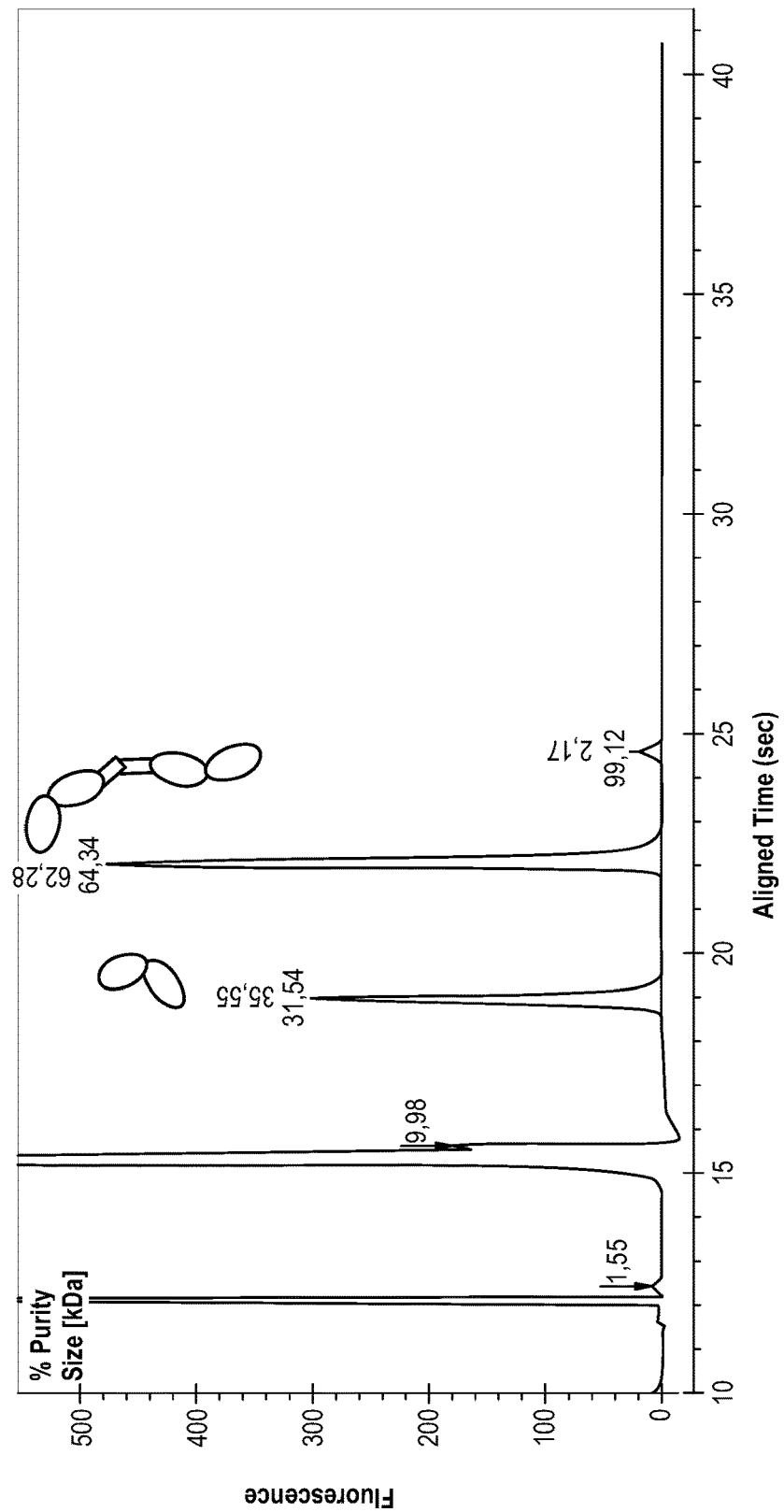
FIG. 19 Reducing CE-SDS analysis of second elution peak from FIG. 17.

As reported for example 5, the load fluid from the production of the bispecific scFab TWEAK-IL17 subsequent to Protein A affinity chromatography contained three protein species: the bispecific antibody, the anti-IL17 homodimer and a 5/4 antibody. The load fluid was subjected to cation exchange chromatography and eluted using a linear salt gradient as represented in FIG. 17. The protein from the load fluid eluted in two peaks (FIG. 17). CE-SDS analysis of the pooled fractions of the first peak revealed that they contained the bispecific antibody and the 5/4 antibody species (see, example 5 and FIG. 18 (CE-SDS under non-reducing conditions)). CE-SDS analysis of the pooled fractions of the second peak revealed that they contained exclusively the IL-17 homodimer (see, FIG. 19, CE-SDS under reducing conditions). Thus, the use of the cation exchange column allowed the ready separation of bispecific antibody and/or 5/4 antibody contaminant species from the homodimer molecules. Example 5 demonstrates that the coeluted bispecific antibody and 5/4 antibody contaminant can then be readily separated using hydroxyapatite chromatography as described herein. The differences in the results of examples 5 and 6 provide further evidence that that hydroxyapatite chromatographic methods as described herein provide a unique chromatographic tool, distinct from previous methods known in the art, e.g., ion-exchange chromatography.

Accordingly, the use of hydroxyapatite chromatography as described herein, optionally in combination with other chromatographic methods allows the separation of bispecific antibodies from byproducts specific to bispecific antibody production.

The invention claimed is:

1. A method of separating a bispecific antibody comprising an Fc domain from a solution comprising said bispecific antibody, said method comprising
    (a) contacting said solution with a hydroxyapatite chromatography medium,
        wherein said solution further comprises
            (i) one or more fragments of said bispecific antibody, which one or more fragments comprise an Fc domain, and/or
            (ii) one or more bispecific antibody specific byproducts (BASBs) having a heterodimer or homodimer of antibody heavy chains, a single antibody light chain and a Fab or scFab fragment, which one or more BASBs comprise an Fc domain;
    (b) adsorbing said bispecific antibodies to said hydroxyapatite chromatography medium, and
    (c) eluting said bispecific antibody from said hydroxyapatite chromatography medium in the presence of chloride ions,
wherein said eluting comprises
    (i) a starting composition of elution buffer having a pH of 6.5 to 8.0, a phosphate ion concentration of between about 1 mM and about 20 mM, a calcium ion concentration of between about 0.001 mM and about 0.5 mM and a chloride ion concentration of between about 10 mM and about 200 mM
    (ii) increasing the chloride ion concentration of said starting composition according to a gradient; and
    (iii) obtaining an eluate fraction, which fraction contains said bispecific antibody but does not contain at least one of said one or more fragments and/or does not contain at least one of said one or more BASBs.

2. The method according to claim 1, wherein said at least one of said one or more fragments is a ½ antibody or a ¾ antibody; or wherein said at least one of said one or more polypeptides is a 5/4 antibody.

3. The method according to claim 1, wherein said eluting is in the presence of an elution buffer having a pH of 6.5 to 7.5, a phosphate ion concentration of about 10 mM, a calcium ion concentration of about 0.1 mM and a chloride ion concentration of 50 mM, wherein the concentration of chloride ions is increased in a gradient from about 50 mM to about 500 mM.

4. The method according to claim 3, wherein said gradient is a linear gradient, a stepwise gradient, or a combination thereof in a linear-stepwise gradient.

5. The method according to claim 1, wherein said solution comprises the bispecific antibody-containing fraction or pooled bispecific antibody containing fractions from the eluate of an affinity chromatography medium having specificity for at least one of an antibody Fc domain, a kappa domain of an antibody light chain, and a lambda domain of an antibody light chain.

6. The method according to claim 1, wherein said method further comprises an upstream or downstream ion exchange chromatography process, which process separates said bispecific antibody from at least one of said fragments, said polypeptides, and a ½ antibody homodimer.

7. The method according to claim 6, wherein said ion exchange chromotography process is a cation exchange unit operation.

8. The method according to claim 1, wherein said bispecific antibody is a CrossMab bispecific antibody or wherein one of the heavy chains of said bispecific antibody comprises a scFab.

9. The method according to claim 1, wherein said bispecific antibody is a knob-in-hole (KiH) bispecific antibody.

10. The method according to claim 1, wherein said bispecific antibody is a CrossMab and KiH bispecific antibody, and wherein said bispecific antibody has specificity for EGFR and IGFR, or has specificity for Ang2 and VEGF.

11. The method according to claim 1, wherein one of the heavy chains of said bispecific antibody comprises a scFab, wherein said bispecific antibody is a KiH bispecific antibody, and wherein said bispecific antibody has specificity for the combination of
Ang2 and VEGF,
EGFR and IGFR, or
TWEAK and IL17.

* * * * *